US009375150B2

(12) United States Patent
Jarrell et al.

(10) Patent No.: US 9,375,150 B2
(45) Date of Patent: Jun. 28, 2016

(54) IDENTIFICATION OF PRESSURE CUFF CONDITIONS USING FREQUENCY CONTENT OF AN OSCILLOMETRIC PRESSURE SIGNAL

(75) Inventors: Kenneth E. Jarrell, Littleton, CO (US); David C. Jones, Evergreen, CO (US)

(73) Assignee: Summit Doppler Systems, Inc., Golden, CO (US)

( * ) Notice: Subject to any disclaimer, the term of this patent is extended or adjusted under 35 U.S.C. 154(b) by 1100 days.

(21) Appl. No.: 13/455,967

(22) Filed: Apr. 25, 2012

(65) Prior Publication Data
US 2013/0289421 A1 Oct. 31, 2013

(51) Int. Cl.
*A61B 5/02* (2006.01)
*A61B 5/00* (2006.01)
*A61B 5/022* (2006.01)

(52) U.S. Cl.
CPC ......... *A61B 5/02007* (2013.01); *A61B 5/02225* (2013.01); *A61B 5/6824* (2013.01); *A61B 5/6829* (2013.01); *A61B 5/7257* (2013.01)

(58) Field of Classification Search
CPC ...................................................... A61B 5/022
See application file for complete search history.

(56) References Cited

U.S. PATENT DOCUMENTS

| | | |
|---|---|---|
| 4,037,325 A | 7/1977 | Weber et al. |
| 4,807,638 A | 2/1989 | Sramek |
| 4,926,874 A | 5/1990 | Lee |
| 4,998,534 A | 3/1991 | Claxton, III et al. |
| 5,050,613 A | 9/1991 | Newman et al. |
| 5,103,827 A | 4/1992 | Smith |
| 5,154,680 A | 10/1992 | Drzewiecki et al. |
| 5,158,091 A | 10/1992 | Butterfield et al. |
| 5,195,522 A | 3/1993 | Pytel et al. |

(Continued)

FOREIGN PATENT DOCUMENTS

| | | |
|---|---|---|
| EP | 1715429 | 10/2006 |
| JP | 5176900 | 7/1993 |
| JP | 2003342546 | 12/2002 |

OTHER PUBLICATIONS

"Harmonic Analysis of Noninvasively Recorded Arterial Pressure Waveforms in Healthy Bonnet Macaques (Macaca radiate)" by Olafiranye et al., Journal of the American Association for Laboratory Animal Science, pp. 79-83, Jan. 2011.*

(Continued)

*Primary Examiner* — Patricia Mallari
*Assistant Examiner* — Vasuda Ramachandran
(74) *Attorney, Agent, or Firm* — Fish & Richardson P.C.

(57) ABSTRACT

A method, system and computer program product are provided for evaluating whether an oscillometric signal representative of pressure oscillations in the vasculature of a patient is associated with special conditions that may lead to inadvertently identifying the signal as being indicative of peripheral arterial disease or non-analyzable. In one embodiment, the method includes obtaining an oscillometric signal at a location on an extremity of the patient, determining a ratio using a value associated with a first frequency component of the oscillometric signal and a value associated with a second frequency component of the oscillometric signal, comparing the ratio to a threshold value, associating a first diagnostic class with the oscillometric signal when a first outcome results from comparing the ratio to a threshold value, and associating a second diagnostic class with the oscillometric signal when a second outcome results from comparing the ratio to a threshold value.

11 Claims, 12 Drawing Sheets

(56) References Cited

U.S. PATENT DOCUMENTS

| | | | |
|---|---|---|---|
| 5,261,412 A | 11/1993 | Butterfield et al. | |
| 5,271,405 A | 12/1993 | Boyer et al. | |
| 5,273,046 A | 12/1993 | Butterfield et al. | |
| 5,284,150 A | 2/1994 | Butterfield et al. | |
| 5,363,855 A | 11/1994 | Drzewiecki et al. | |
| 5,379,028 A | 1/1995 | Chung | |
| 5,379,770 A | 1/1995 | Van Veen | |
| 5,402,585 A | 4/1995 | Lund | |
| 5,439,001 A | 8/1995 | Butterfield et al. | |
| 5,509,416 A | 4/1996 | Wilmott | |
| 5,582,176 A | 12/1996 | Swerling et al. | |
| 5,590,649 A | 1/1997 | Caro et al. | |
| 5,605,156 A | 2/1997 | Drzewiecki et al. | |
| 5,617,867 A | 4/1997 | Butterfield et al. | |
| 5,640,960 A | 6/1997 | Jones et al. | |
| 5,715,826 A | 2/1998 | Horrocks et al. | |
| 5,803,917 A | 9/1998 | Butterfield | |
| 5,827,223 A | 10/1998 | Butterfield | |
| 5,908,027 A | 6/1999 | Butterfield et al. | |
| 6,146,336 A | 11/2000 | Paulat | |
| 6,149,587 A | 11/2000 | Raines | |
| 6,158,965 A | 12/2000 | Butterfield et al. | |
| 6,213,972 B1 | 4/2001 | Butterfield et al. | |
| 6,290,650 B1 | 9/2001 | Butterfield et al. | |
| 6,336,044 B1 | 1/2002 | Ghiassi et al. | |
| 6,358,225 B1 | 3/2002 | Butterfield | |
| 6,416,291 B1 | 7/2002 | Butterfield et al. | |
| 6,641,540 B2 | 11/2003 | Fleischman et al. | |
| 6,726,632 B2 | 4/2004 | Tampo et al. | |
| 6,733,460 B2 | 5/2004 | Ogura | |
| 6,740,042 B1 | 5/2004 | Lerner et al. | |
| 6,758,820 B2 | 7/2004 | Narimatsu et al. | |
| 6,796,946 B2 | 9/2004 | Ogura et al. | |
| 6,843,772 B2 | 1/2005 | Nunome et al. | |
| 6,893,401 B2 | 5/2005 | Chen et al. | |
| 6,923,771 B2 | 8/2005 | Ogura et al. | |
| 7,074,188 B2 | 7/2006 | Nair et al. | |
| 7,166,076 B2 | 1/2007 | Poliac et al. | |
| 7,172,555 B2 | 2/2007 | Poliac et al. | |
| 7,175,597 B2 | 2/2007 | Vince et al. | |
| 7,214,192 B2 | 5/2007 | Poliac et al. | |
| D554,267 S | 10/2007 | Cohen | |
| 7,300,404 B1 | 11/2007 | Kolluri et al. | |
| 7,549,964 B2 | 6/2009 | Kolasa et al. | |
| D608,010 S | 1/2010 | Moscovita et al. | |
| D610,260 S | 2/2010 | Moscovita et al. | |
| D616,100 S | 5/2010 | Moscovita et al. | |
| D620,121 S | 7/2010 | Moscovita et al. | |
| D629,522 S | 12/2010 | Moscovita et al. | |
| D630,331 S | 1/2011 | Moscovita et al. | |
| 7,899,224 B2 | 3/2011 | Nair et al. | |
| 7,927,275 B2 | 4/2011 | Kuban et al. | |
| 7,940,969 B2 | 5/2011 | Nair et al. | |
| 7,983,930 B1 | 7/2011 | Romans | |
| 8,628,477 B2 | 1/2014 | Addison et al. | |
| 2002/0045806 A1 | 4/2002 | Baker et al. | |
| 2005/0086817 A1 | 4/2005 | Ramsthaler | |
| 2005/0155246 A1 | 7/2005 | Montagnino | |
| 2008/0076984 A1 | 3/2008 | Gough | |
| 2008/0235058 A1 | 9/2008 | Friedman | |
| 2009/0036778 A1 | 2/2009 | Cohen et al. | |
| 2009/0036786 A1 | 2/2009 | Gough et al. | |
| 2009/0099461 A1 | 4/2009 | Jones et al. | |
| 2009/0099463 A1 | 4/2009 | Jones et al. | |
| 2009/0099465 A1 | 4/2009 | Jones et al. | |
| 2009/0209868 A1 | 8/2009 | Hersh et al. | |
| 2010/0292586 A1 | 11/2010 | Rooke et al. | |
| 2011/0172540 A1 | 7/2011 | Jackson | |
| 2011/0237962 A1* | 9/2011 | Hersh | A61B 5/0225 600/493 |
| 2011/0306893 A1 | 12/2011 | Harrold et al. | |

OTHER PUBLICATIONS

"Oscillometry," Medical Electronics, Dr. Neil Townsend, Michaelmas Term 2001, pp. 48-54.

"Performance of the CAS Oscillometric Algorithm When Compared Against Various Commercially Available NIBP Simulators," CAS Medical Systems, Inc., Oct. 4, 2007, pp. 1-9.

Barbé et al., "Oscillometric Blood Pressure Measurements: A Signal Analysis," Journal of Physics: Conference Series, vol. 238, No. 1, pp. 1-6, Jul. 1, 2010.

Geddes, L.A. Handbook of Blood Pressure Measurement. The Humana Press Inc. 27 pages. 1991.

Gornik et al., "Validation of a Method for Determination of the Ankle-Brachial Index in the Seated Position," Journal of Vascular Surgery, vol. 48, No. 5, pp. 1204-1210, Nov. 2008.

Invitation to Pay Additional Fees, Application No. PCT/US2011/052700; mailed Jan. 30, 2012.

Jazbinsek et al., "Influence of Different Presentations of Oscillometric Data on Automatic Determination of Systolic and Diastolic Pressures," Annals of Biomedical Engineering, vol. 38, No. 3, pp. 774-787, Dec. 2, 2009.

Vantage ABI User Manual, Summit Doppler Systems, Inc., pp. 1-43.

Vista AVS User Manual, Summit Doppler Systems, Inc., pp. 1-68.

Gornik et al., "Novel Oscillometric-Based Algorithm for Diagnosis of Peripheral Artery Disease (PAD) and Determination of the Ankle-Brachial Index (ABI)," Oscillo Poster, Cleveland Ohio, p. 1.

Ramsey et al., Toe blood pressure. A valuable adjunct to ankle pressure measurement for assessing peripheral arterial disease, The Journal of Cardiovasucular Surgery, 1983, 24(1), Abstract.

* cited by examiner

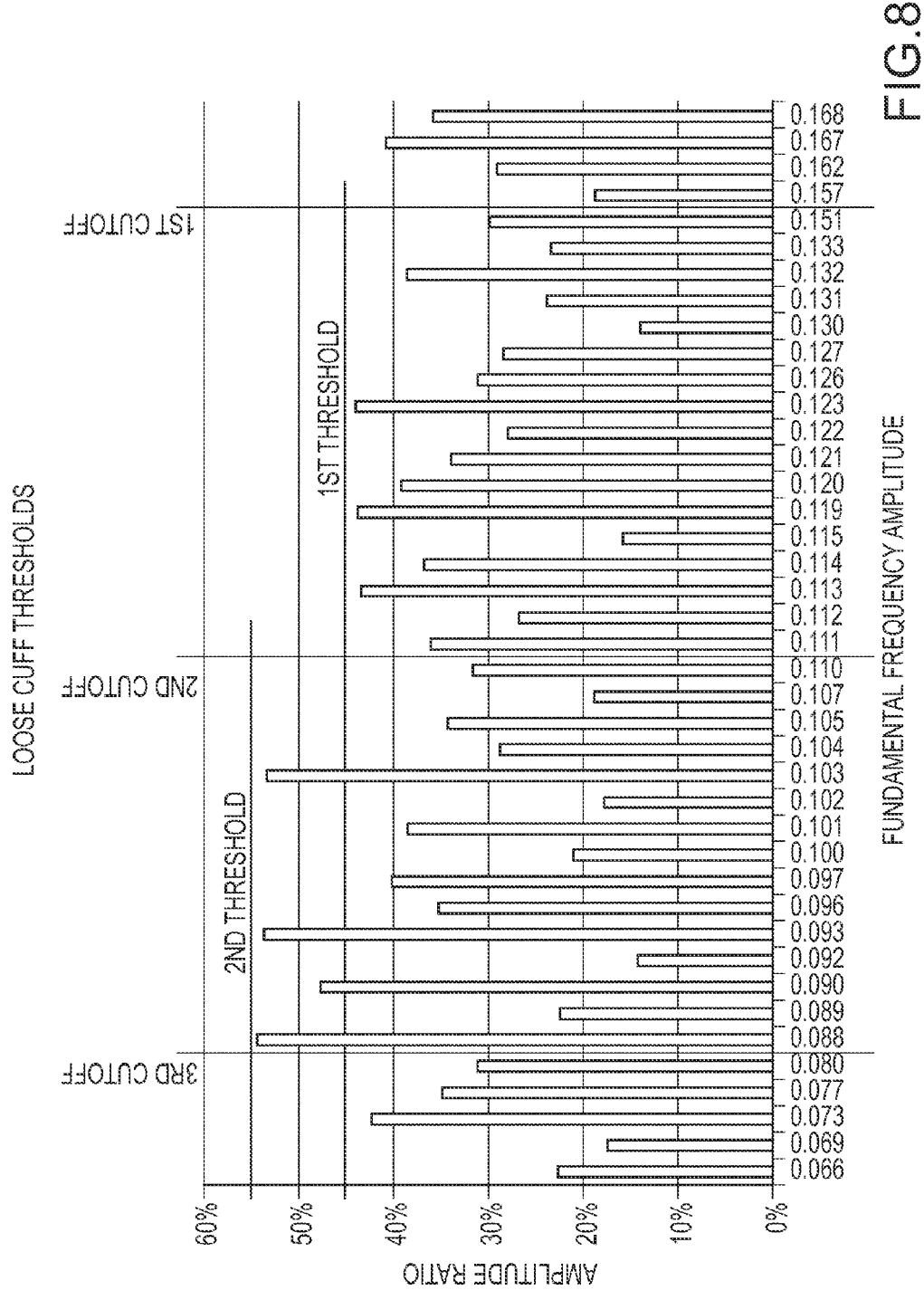

IDENTIFICATION OF PRESSURE CUFF CONDITIONS USING FREQUENCY CONTENT OF AN OSCILLOMETRIC PRESSURE SIGNAL

BACKGROUND

Atherosclerosis of the lower extremities, also known as peripheral arterial disease (PAD), is a highly prevalent condition affecting about 5% of adults over 50 years of age and about 15% of adults over 70 years of age in the United States. A typical symptom of PAD is pain in the legs during exertion that is relieved with rest. However, other degrees of PAD are possible ranging from mild to severe. Patients with PAD may be entirely asymptomatic.

One method of diagnosing PAD is to compare the blood pressure values from two patient extremities in the upper and lower limbs (e.g., leg and arm blood pressure values). This method is generally referred to herein as an extremity blood pressure ratio (EBPR) examination. The most common EBPR examination for the diagnosis of PAD is the ankle brachial index (ABI) examination. The ABI exam compares a blood pressure value from the brachial artery in a patient's arm with a blood pressure value from the patient's ankle. When the ankle and arm systolic pressure values are obtained, the ratio of ankle pressure to arm pressure is normally greater than 1.0. An ankle/brachial ratio (ABI) that is 0.9 or less is considered abnormal and indicates the presence of significant PAD in the patient. The ABI value may reflect the severity of PAD in the index limb (for example ABI values of 0.9-0.7 are consistent with mild disease, ABI values of 0.7-0.4 are consistent with moderate disease, and ABI values of less than 0.4 are consistent with severe PAD).

A variety of techniques may be used in order to determine blood pressure values for an EBPR procedure. For example, a sphygmomanometer (e.g., a blood pressure cuff) may be placed around an extremity of the patient and inflated to occlude blood flow through an artery. A trained health care provider may, for example, use a stethoscope to listen for Korotcoff sounds associated with the return of blood flow in the artery during deflation of the blood pressure cuff to determine systolic and diastolic pressure within the artery. Other techniques to determine blood pressure values have been developed that may employ a Doppler ultrasound blood flow detector rather than a stethoscope to determine when blood flow returns to the artery (systolic pressure). However, the use of a Doppler ultrasound blood flow detector still requires trained health care providers in order to operate the detector correctly.

Another technique for determining an indicated blood pressure value includes obtaining a pressure signal that oscillates in a manner that corresponds to fluctuations in limb blood volume during deflation of a blood pressure cuff as blood flow returns to an occluded artery. This signal may be referred to as an oscillometric signal. The oscillometric signal can be processed to obtain a mean arterial pressure (MAP) and indicated values of systolic and diastolic pressure. This practice has been widely accepted for measurement of blood pressure in the arms of patients in clinical practice. However, use of the oscillometric technique for determining blood pressures in the lower extremities of patients has been questioned, particularly in cases where the patient is suffering from some degree of PAD.

SUMMARY

Against this background, it has been recognized by the present inventor(s) that the use of oscillometric techniques may be beneficial for use in the evaluation of patients (e.g., for evaluation of PAD in patients). The use of oscillometric techniques may be accomplished by personnel lacking the skill level and special training needed for traditional means of measuring blood pressure values (e.g., using a stethoscope, Doppler ultrasound blood flood detector, or the like). It has been further recognized by the present inventor(s) that it is desirable to provide safeguards against errors associated with the performance of an oscillometric analysis. For example, because persons lacking skill and special training may implement oscillometric techniques, incorrectly located pressure applicators, misapplied pressure applicators, and the like may interfere with obtaining a reliable oscillometric signal. Another issue that may interfere with obtaining a reliable oscillometric signal is a pressure applicator that is too loose around the extremity (e.g. the upper arm or the lower leg/ankle of the patient). This may occur where the pressure applicator is not wrapped tightly enough prior to inflation and/or where the pressure applicator is oversized compared to the location on the extremity at which the applicator is applied. These and other such situations may be referred to herein as special cuff conditions. The present inventor(s) have recognized that special cuff conditions may affect characteristics of the oscillometric signal obtained from an otherwise healthy patient such as reducing the amplitude of the fundamental frequency of the oscillometric signal. A reduced amplitude of the fundamental frequency of the oscillometric pressure signal may also be associated with the presence of disease in the patient. Accordingly, the present inventor(s) have recognized that by evaluating the frequency content of the oscillometric pressure signal, the presence of special cuff conditions can be identified resulting in an improved oscillometric pressure signal analysis.

Accordingly, a first aspect includes a method for evaluating whether an oscillometric signal representative of pressure oscillations in the vasculature of a patient is associated with special conditions. The method may include obtaining an oscillometric signal at a location on an extremity of the patient. A ratio may be determined using a value associated with a first frequency component of the oscillometric signal and a value associated with a second frequency component of the oscillometric signal. The ratio may be compared to a threshold value. When a first outcome of the comparison to the threshold value results from comparing the ratio to a threshold value, a first diagnostic class from a plurality of diagnostic classes may be associated with the oscillometric signal. When a second outcome of the comparison to the threshold value results from comparing the ratio to a threshold value, a second diagnostic class from a plurality of diagnostic classes may be associated with the oscillometric signal.

In a second aspect, a system operable to evaluate whether an oscillometric signal representative of pressure oscillations in the vasculature of a patient is associated with special conditions may include a pressure applicator, a processor in operative communication with the pressure applicator, a pressure transducer in operative communication with the processor, and a special conditions evaluation module. The pressure applicator may be positionable at a location on an extremity of a patient. The pressure applicator may also be controllable to apply a pressure to occlude blood flow in a portion of the extremity and to reduce the pressure applied thereby to permit blood flow to return in the portion of the extremity. The pressure transducer may be in operative communication with the pressure applicator to obtain an oscillometric signal from the extremity as pressure applied by the pressure applicator to the extremity is reduced. The special conditions evaluation module may be executable by the processor to: determine a ratio using a value associated with a first frequency component of the oscillometric signal and a value associated with a second frequency component of the oscillometric signal; compare the ratio to a threshold value; associate a first diagnostic class from a plurality of diagnostic classes with the oscillometric signal when a first outcome of the comparison to the threshold value results from comparing the ratio to a threshold value; and associate a second diagnostic class from a plurality of diagnostic classes with the oscillometric signal when a second outcome of the comparison to the threshold value results from comparing the ratio to a threshold value.

In a third aspect, a computer program product for evaluating whether an oscillometric signal representative of pressure oscillations in the vasculature of a patient is associated with special conditions includes a computer readable medium having computer readable program code embodied therein. The computer readable program code may include computer readable program code enabling a processor to obtain an oscillometric signal at a location on an extremity of the patient. The computer readable program code may also include computer readable program code enabling a processor to determine a ratio using a value associated with a first frequency component of the oscillometric signal and a value associated with a second frequency component of the oscillometric signal. The computer readable program code may further include computer readable program code enabling a processor to compare the ratio to a threshold value. The computer readable program code may additionally include computer readable program code enabling a processor to associate a first diagnostic class from a plurality of diagnostic classes with the oscillometric signal when a first outcome of the comparison to the threshold value results from comparing the ratio to a threshold value. The computer readable program code may also include computer readable program code enabling a processor to associate a second diagnostic class from a plurality of diagnostic classes with the oscillometric signal when a second outcome of the comparison to the threshold value results from comparing the ratio to a threshold value.

Various refinements exist of the features noted in relation to the various aspects of the present invention. Further features may also be incorporated in the various aspects of the present invention.

For example, in one embodiment, a transform of an oscillometric pressure signal may be performed. The transform may be a Fourier transform, an RMS calculation, or other appropriate mathematical transform. The transform may be used to assist in analyzing an oscillometric signal in the aspects recited above. For instance, the transform may produce a frequency domain representation of the oscillometric pressure signal. In one embodiment, the transform is performed on a window of interest of an oscillometric pressure signal (e.g., such as a portion of the signal surrounding a maximum amplitude of the oscillometric pressure signal). The value associated with a first frequency component of the oscillometric signal may, for example, be a maximum amplitude value at a fundamental frequency component of the frequency domain representation of the oscillometric signal, the value associated with a second frequency component of the oscillometric signal may, for example, be an amplitude value at a second harmonic frequency component of the frequency domain representation of the oscillometric signal, and the ratio may, for example, be determined by dividing the amplitude value associated with the second harmonic frequency by the amplitude value associated with the fundamental frequency component.

These refinements and additional features may exist individually or in any combination, and various features of the various aspects may be combined. These and other aspects and advantages of the present invention will be apparent upon review of the following Detailed Description when taken in conjunction with the accompanying figures.

BRIEF DESCRIPTION OF THE DRAWINGS

For a more complete understanding of the present invention and further advantages thereof, reference is now made to the following Detailed Description, taken in conjunction with the drawings, in which:

FIG. 8 is a plot of the ratio of the second harmonic frequency amplitude to the fundamental frequency amplitude versus the fundamental frequency amplitude for lower extremity oscillometric signals obtained from a sample population of patients.

DETAILED DESCRIPTION

Figure 1:
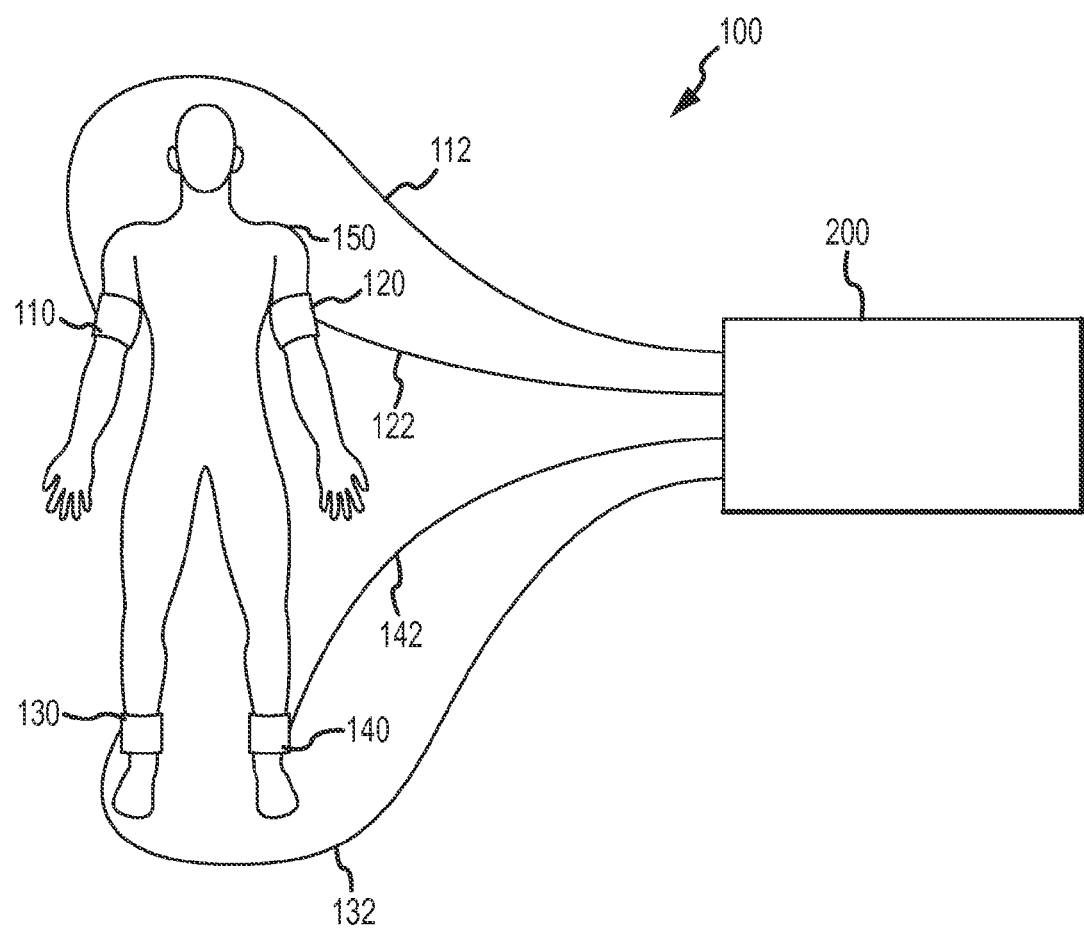
FIG. 1 is a schematic view of an embodiment of a system operable to determine one or more indicated blood pressure values in various extremities of a patient and an ABI.

FIG. 1 is a schematic view of an embodiment of a system 100 operable to determine one or more indicated blood pressure values in a patient 150. The system 100 may include a number of pressure applicators that may be positioned at various locations with respect to the patient 150. The pressure applicators may be operable to occlude blood flow in the vasculature (e.g., arteries) of the patient adjacent to the pressure applicator. In one embodiment, the pressure applicators may be controllably inflatable blood pressure cuffs. Other pressure applicators may be used that are operable to controllably occlude blood flow in the arteries of the patient and controllably release the applied pressure to allow blood flow in the arteries to return.

For instance, in one embodiment, the system may include four cuffs (110, 120, 130, 140) that may be positioned with respect to the arms and legs of the patient 150 on both the right and left sides of the patient 150. In this regard, the system 100 may be operable to determine indicated blood pressure values at each of these corresponding locations. The locations on the patient 150 may broadly be categorized into locations on an upper extremity or a lower extremity of the patient 150. The upper extremity of the patient generally refers to the arms, head, and upper torso of the patient 150, while the lower extremity of the patient generally refers to the legs and lower body of the patient 150.

Specifically, the system 100 may include a first cuff 110 positionable on the right arm of the patient 150. The first cuff 110 may be in fluid communication with a control module 200 by way of first pneumatic tubing 112 such that the first cuff 110 is inflatable to controllably occlude the blood flow in the portion of the right arm of the patient 150 adjacent to the first cuff 110. For example, the flow of blood in the brachial artery in the patient's right arm may be occluded by inflating the first cuff 110. In other embodiments, a cuff (not shown) may be in operative communication with the control module 200 such that only data collected by the cuff is transmitted and no fluid communication is provided between the cuff and the control module 200. For example, the cuff itself may include a controller that controls inflation and deflation of the cuff without being in fluid communication with the control module 200. The cuff may be in operative communication with the control module 200 such that data may be passed between the cuff and the control module 200. For instance, the cuff and control module 200 may include a wireless or wired communications channel to transmit data between the cuff and the control module 200.

A second cuff 120 may be positionable on the left arm of the patient 150. The second cuff 120 may be in fluid communication with the control module 200 by way of second pneumatic tubing 122 such that the second cuff 120 is inflatable to controllably occlude the blood flow in the portion of the left arm of the patient 150 adjacent to the second cuff 120. For instance, the brachial artery in the patient's left arm may be controllably occluded by inflating the second cuff 120. A third cuff 130 may be positionable on the right leg of the patient 150 (e.g., at the patient's ankle). The third cuff 130 may be in fluid communication with the control module 200 by way of third pneumatic tubing 132 such that the third cuff 130 is inflatable to selectively occlude the blood flow in the portion of the right leg of the patient 150 adjacent to the third cuff 130. For example, the third cuff 130 may controllably occlude blood flow in the dorsalis pedis or posterior tibial arteries in the right leg of the patient 150 upon inflation of the third cuff 130. Further still, a fourth cuff 140 may be positionable on the left leg of the patient 150 (e.g., at the left ankle of the patient 150). The fourth cuff 140 may be in fluid communication with the control module 200 by way of fourth pneumatic tubing 142 such that fourth cuff 140 is inflatable to controllably occlude the blood flow in the portion of the left leg of the patient 150 adjacent to the fourth cuff 140. For example, the blood flow in the dorsalis pedis or posterior tibial arteries may be occluded in the left leg of the patient 150 upon inflation of the fourth cuff 140.

The control module 200 may be operable to control the inflation and deflation of each cuff (110, 120, 130, 140) individually. Thus, each cuff (110, 120, 130, 140) may be independently used in determining an indicated blood pressure value at respective locations in the patient corresponding to the location of the cuffs (110, 120, 130, 140). In one embodiment, the cuffs on the right side of the patient (e.g., the first cuff 110 and third cuff 130) may collectively be used in determining an indicated blood pressure value in the upper extremity and an indicated blood pressure value in the lower extremity of the patient 150. Similarly, the left side cuffs (e.g., the second cuff 120 and fourth cuff 140) may collectively be used in determining an indicated blood pressure value in the upper extremity and an indicated blood pressure value lower extremity of the patient 150. In any regard, indicated blood pressure values at each location corresponding to a cuff may be determined.

Figure 2:
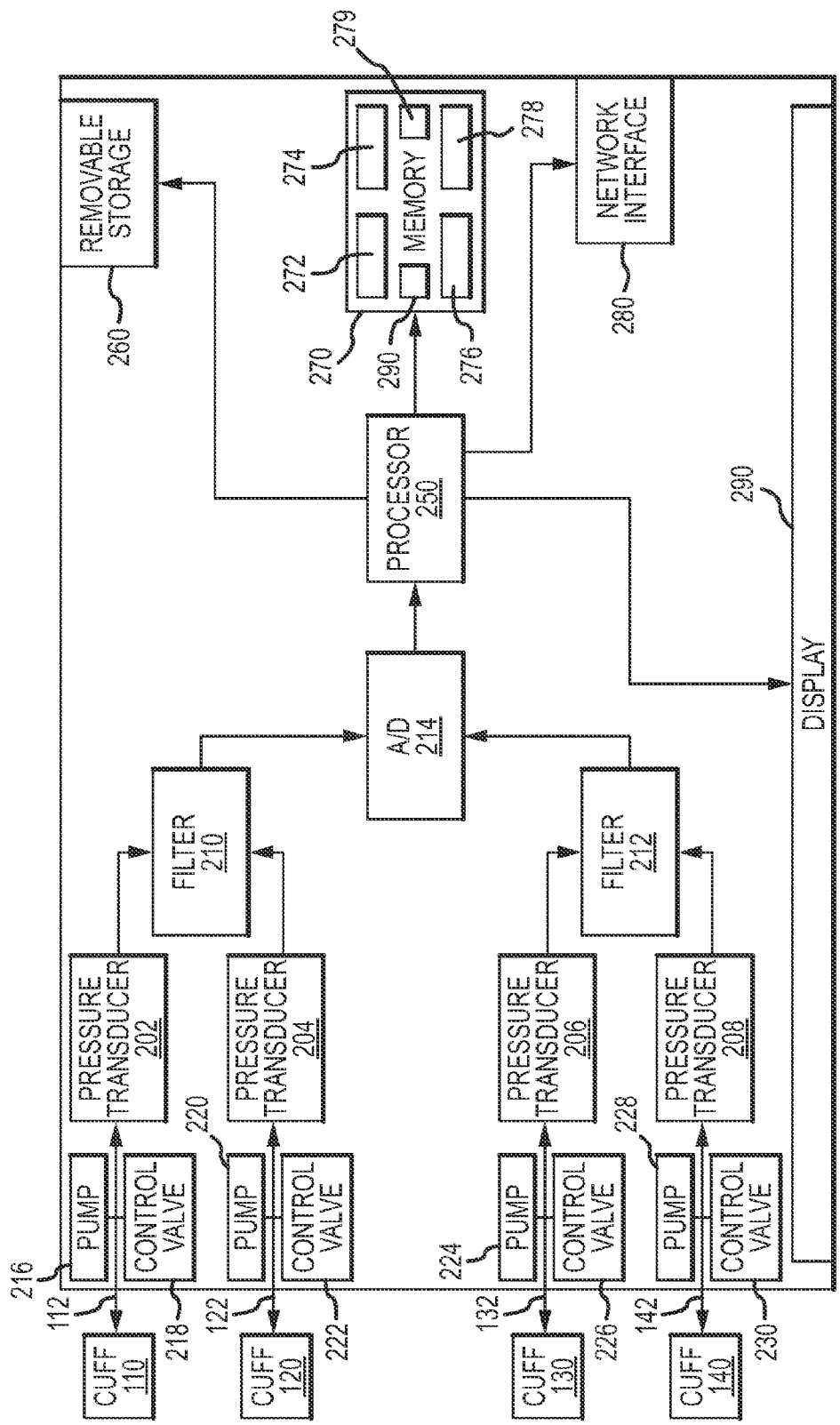
FIG. 2 is a more detailed schematic view of the embodiment of the system shown in FIG. 1 operable to determine one or more indicated blood pressure values in various extremities of a patient and an ABI.

The control module 200 is shown in greater detail in FIG. 2. As described with reference to FIG. 1, the first cuff 110 may be in fluid communication with the control module 200 by way of first pneumatic tubing 112. Also, a first pump 216 and a first control valve 218 may also be in fluid communication with the first cuff 110. In this regard, the first pump 216 may be operable to inflate the first cuff 110 to occlude blood flow at the location of the first cuff 110 as described above. A first pressure transducer 202 may monitor the pressure in the first cuff 110 to prevent over pressurization of the first cuff 110 during inflation. In one embodiment, a maximum upper inflation limit of the first cuff may be about 280 mmHg. The first control valve 218 may be operable to control the pressure in the first cuff 110 so as to decrease the pressure in the first cuff 110 over a period of time. In this regard, the first control valve 218 may decrease the pressure in the first cuff 110 in a substantially linear manner over a desired pressure range (e.g., between an upper inflation pressure limit and a lower deflation pressure limit). In other embodiments, the control valve 218 may decrease the pressure in the first cuff 110 in an incremental, stepwise manner. The first pressure transducer 202 may further be operable to monitor the pressure in the first cuff 110 during the controlled decrease in pressure in the first cuff 210. The instantaneous pressure in the arteries of the patient fluctuates with the heartbeat of the patient, which may influence the pressure in the first cuff 110 as detected by the first pressure transducer 202. This detected fluctuating pressure may produce a pressure signal corresponding to the measured pressure in the first cuff 110. This pressure signal may be normalized to compensate for the gauge pressure in the first cuff 110. Thus, a portion of the pressure signal may be removed to produce an oscillometric pressure signal associated with the location of the first cuff 110.

The second cuff 120, the third cuff 130, and the fourth cuff 140 may also be operated in a manner similar to that described above with regard to the first cuff 110 to produce oscillometric signals associated with the locations corresponding to the second cuff 120, third cuff 130, and fourth cuff 140, respectively. In this regard, the second cuff 120 may be in operative communication with a second pump 220, a second control valve 222, and a second pressure transducer 204. The third cuff 130 may be in operative communication with a third pump 224, a third control valve 226, and a third pressure transducer 206. The fourth cuff 140 may be in operative communication with a fourth pump 228, a fourth control valve 230, and a fourth pressure transducer 208. In other embodiments, more than one cuff may be in operative communication with a single pump, a single control valve, and/or a single pressure transducer. As such, fewer pumps, control valves, and/or pressure transducers may be provided in other embodiments of a control module.

Each of the pressure transducers (202, 204, 206, 208) may be operable to measure a pressure signal observed in a corresponding one of the cuffs (110, 120, 130, 140). The pressure transducers (202, 204, 206, 208) may be analog or digital transducers capable of producing analog or digital outputs. As shown in FIG. 2, the pressure transducers (202, 204, 206, 208) may be analog pressure transducers that provide an analog output corresponding to the measured pressure in each cuff (110, 120, 130, 140).

As discussed above, a cuff (not shown) may be provided that is operative to communicate data to a control module. In this regard, a pump, control valve, and pressure transducer may be provided with the cuff at the location on the patient.

The cuff may comprise a contained unit capable of controlling inflation and deflation of the cuff and monitoring the cuff pressure. As such, data may be transmitted (e.g., via wires or wirelessly) between the control module 200 and the cuff (e.g., the control module 200 may transmit a "start" signal to begin operation of the cuff and the cuff may transmit pressure readings to the control module 200). In this regard, the control module 200 may be a computing device (e.g., a laptop or desktop computer) operable to receive data from and/or transmit data to the cuff. Such a computing device may execute computer readable program code stored on a computer readable medium (e.g. a hard drive, a flash memory, an optical drive, a floppy drive, etc.) in order to perform various processing of the data as described herein.

The control module 200 may include a first filter 210 and a second filter 212. The first filter 210 may be in operative communication with the first pressure transducer 202 and the second pressure transducer 204. The second filter 212 may be in operative communication with the third pressure transducer 206 and the fourth pressure transducer 208. In other embodiments, each pressure transducer may have a separate filter to which the output of the pressure transducer is provided or different arrangements between the pressure transducers and filters may be provided. However, in the embodiment shown in FIG. 2, it may be that only one of the first and second cuffs (110, 120) are inflated at any one time, and only one of the third and fourth cuffs (130, 140) are inflated at any one time. Thus, as discussed above, values may be determined for the left side and right side of the patient separately (e.g., at different instances) such that not all four cuffs (110, 120, 130, 140) are inflated simultaneously.

In any regard, the filters (210, 212) may be operable to perform desired filtering of a received signal (e.g., high pass, low pass, and/or band pass filtering). In the embodiment shown in FIG. 2, this may include providing analog filters capable of filtering analog signals. Additionally or alternatively, digital filtering may be employed to perform the desired filtering of a signal. In this regard, the filters 212 and 214 may comprise hardware filters or software filters capable of performing the desired filtering of the received signal.

The control module 200 may also include an analog to digital (A/D) converter 214. The A/D converter 214 may be operable to digitize an analog signal. The A/D converter 214 may comprise multiple A/D converters that are provided for multiple channels corresponding to multiple pressure signal inputs received from the pressure transducers (202, 204, 206, 208) by way of the filters (212, 214). In turn, the A/D converter 214 may provide a digital signal to a processor 250 included in the control module 200. The digital signal may include a multiplexed signal containing pressure signal data for each pressure transducer (202, 204, 206, 208). In the case where digital pressure transducers are provided, an A/D converter 214 may not be necessary.

The processor 250 may comprise one or more processors operable to control various functionalities of the system 100. For example, the processor 250 may include one or more general purpose microprocessors capable of executing machine readable code stored on a memory 270 in operative communication with the processor 250. The processor 250 may, for example, include one or more application specific integrated circuits (ASICs). The processor 250 may, for example, include one or more field programmable gate arrays (FPGAs). Further still, a combination of the foregoing (general purpose microprocessors, ASICs, FPGAs) may be employed. In the case where multiple processors are provided, the multiple processors may include individual processors dedicated to specific functionalities of the system 100. For instance, a processor may be provided for performing mathematical transforms (e.g., a Fourier transform) of signals as will be discussed further below. Additionally, individual processors may be provided that include video control processors, interface control processors, pressure check processors, or other specific functionalities provided by specific processors.

Further still, various modules may be provided that are executable by the processor 250 to perform various functionalities of the system 100. For instance, in one embodiment of the system 100, a blood pressure determination module 272 may be provided. The blood pressure determination module 272 may be operable to perform various operations on an oscillometric signal to obtain an indicated blood pressure value at least partially based on the oscillometric signal. The operation associated with the blood pressure determination module 272 is described in greater detail below. Additionally, a selection module 274 may be executable by the processor 250. The selection module 274 may be operable to select an appropriate characteristic ratio from a plurality of ratio values based on the classification of a patient into one of a plurality of diagnostic classes. Again, the operation associated with the selection module 274 is described in further detail below. Also, a transform module 276 may be executable by the processor 250. The transform module 276 may be operable to transform an oscillometric signal utilizing a mathematical transform. The operation associated with the transform module 276 is described in greater detail below. Additionally, a classification module 278 may be executable by the processor 250. The classification module 278 may be operable to classify a patient into a diagnostic class. For instance, the classification module 278 may analyze an oscillometric signal to classify a patient into a diagnostic class. The operation of the classification module 278 is described in greater detail below. These modules may be provided as hardware (e.g., ASICs, FPGAs, etc.) and/or as software in the form of machine readable code stored on the memory 270 and executable by the processor 250, as is depicted in FIG. 2.

The control module 200 may further include a removable storage interface 260. The processor 250 may be in operative communication with the removable storage interface 260 to transfer data thereto. As such, data may be transferred between the system 100 and a removable storage medium (not shown) that may in turn be transported to and used by other devices.

Also, the control module 200 may include a network interface 280. The network interface 280 may be a wired or wireless interface capable of communicating with a network (e.g. a wide area network, a local area network, an intranet, the Internet, etc.). In this regard, the control module 200 may be operable to receive data (e.g., patient data) by way of the network interface 280 and/or transmit data (e.g., patient data) via the network interface 280.

The control module 200 may also include a display 290. The processor 250 may be in operative communication with the display 290 to control the functionality thereof. The display 290 may be operable to display information including, but not limited to, the status of the system 100, indicated blood pressure values obtained at locations of the patient corresponding to the cuffs (110, 120, 130, 140), ratios of various indicated blood pressure values, error messages, or other pertinent data. The display 290 may be a touch screen display operable to also receive inputs from a user. The system 100 may also include a separate input device (not shown) operable to receive inputs from a user.

The system 100 may be operable to determine an indicated blood pressure value at each location at which a cuff (110, 120, 130, 140) is attached. An indicated blood pressure value for each location may be determined by performing one or more analytical processes on an oscillometric pressure signal obtained at each respective location by monitoring oscillations of the pressure in the corresponding cuff as the cuff is deflated and blood flow returns to the vasculature adjacent to the cuff. While some prior systems may have employed oscillometric techniques to arrive at an indicated blood pressure value in the brachial artery of a patient, such prior oscillometric techniques have been found to be inadequate to determine indicated blood pressure values in the lower extremities of patients. A description of an oscillometric technique that overcomes the inadequacies of prior systems is presented below.

Figure 3A:
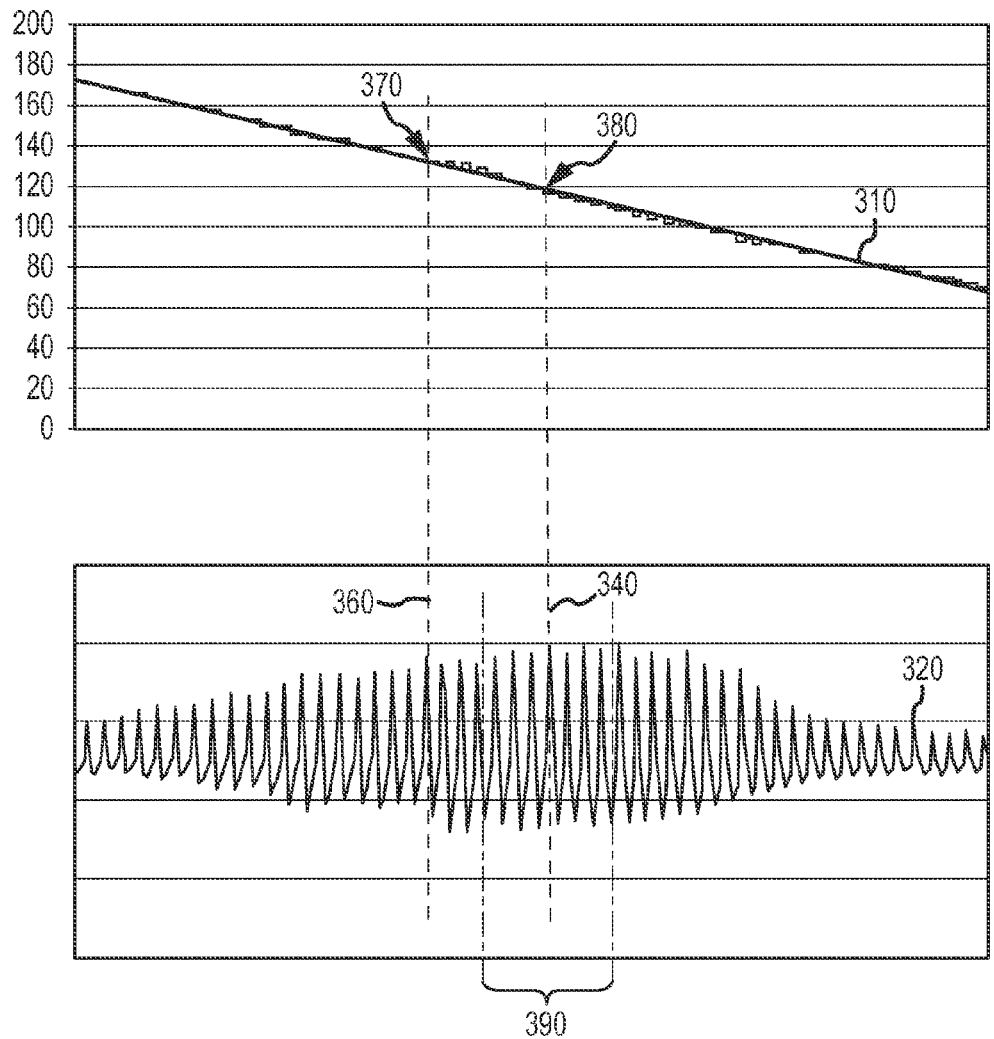
FIG. 3A is a graphical representation of an exemplary cuff pressure curve and oscillometric signal useful for determining an indicated blood pressure value in an extremity of a patient.

FIG. 3A depicts a graphical representation of an exemplary oscillometric signal 320 associated with a location on an extremity of a patient. The graphical representation depicted in FIG. 3A may not be to scale. In the top portion of FIG. 3A, cuff pressure curve 310 indicates the pressure over time in the cuff. In order to obtain the oscillometric signal 320 shown in the bottom portion of FIG. 3A, the pressure in the cuff is generally raised to a level above that of the systolic blood pressure. As such, the cuff may occlude blood flow in the portion of the patient adjacent to the cuff. While the blood flow is occluded in the adjacent portion, the patient's pulsatile arterial flow causes oscillations in the pressure 310 within the cuff. The pressure signal obtained from the cuff may be normalized to remove the portion of the signal attributable to the gauge pressure in the cuff. The result may be a normalized oscillometric pressure signal 320. The pressure 310 within the cuff may be incrementally lowered such that once the pressure in the vasculature of the patient is greater than the cuff pressure 310, blood flow returns to the vasculature of the patient adjacent to the cuff. This may result in a change in amplitude of the oscillatory signal 320. It has been found that the amplitude of the oscillometric signal 320 is typically at a maximum amplitude 340 when the cuff pressure 310 is at the mean arterial pressure (MAP) 380 of the patient's vasculature adjacent to the cuff. Thus, determining the maximum amplitude 340 of the oscillometric signal allows for correlation with the cuff pressure 310 to arrive at the patient's MAP 380 in the location adjacent to the cuff.

In addition, a characteristic ratio may be applied to the maximum amplitude 340 of the oscillometric signal 320 to arrive at an adjusted amplitude value 360. This adjusted amplitude value 360 may be located within the oscillometric signal 320. The adjusted amplitude value 360 may then be correlated to the cuff pressure 310 to arrive at an indicated blood pressure value 370. For instance, for a brachial blood pressure measurement, standard characteristic ratios have been established to produce accurate indications of systolic blood pressure values (e.g., a characteristic ratio of 0.50 of the MAP amplitude may be used to obtain a systolic brachial blood pressure indication). In this regard, the adjusted amplitude value 360 may, at least in part, depend upon the characteristic ratio applied to the maximum amplitude 340.

However, characteristic ratios used for the upper extremities of a patient do not always remain accurate if used for the lower extremities. Moreover, some prior attempts to arrive at a single characteristic ratio for determining an indicated blood pressure value at the lower extremity of patients have failed.

The system 100 shown and described above may be operable to perform a process whereby an oscillometric signal obtained at the lower extremity of a patient is analyzed (e.g., by a selection module and/or classification module) and used to classify the patient into one of at least two diagnostic classes. In the case where the oscillometric signal is associated with a lower extremity location, a different ratio value may be provided for each diagnostic class. Thus, an indicated blood pressure for the lower extremity may be determined utilizing a selected lower extremity characteristic ratio that is selected from a plurality of ratio values at least partially based on the diagnostic class into which the patient is classified. Once the indicated blood pressure value for the lower extremity has been derived, it may be used in an EBPR examination. For instance, an ankle-brachial pressure index (ABI) may be calculated. The ABI may be useful in determining the presence and/or severity of PAD in a patient.

The lower extremity characteristic ratio for each diagnostic class may, for example, be empirically derived. For instance, a study was conducted with patients whose diagnostic class was established as being in one of a plurality of classes (e.g., patients with severe/moderate PAD in one class and patients with mild/no PAD in a second class). The patients were tested using a Doppler based technique to determine blood pressure values at a location at the lower extremity of the patient. An oscillometric signal was also obtained for each patient at the same location. Corresponding data from the Doppler based technique and the oscillometric technique were correlated and statistical methods were employed (e.g., a linear regression) to define a relationship between the collected data. Other statistical methods (e.g., methods other than a linear regression) may have been employed to arrive at a definition of the relationship of the data. The data obtained via the Doppler based technique and the oscillometric technique may be plotted such that the amplitude of the oscillometric signal at the Doppler systolic pressure is represented on the x-axis and the maximum amplitude of the oscillometric signal is represented on the y-axis. In this regard, a best fit line may be established on the plot such that the slope of this best fit line represents the best fit characteristic ratio for the data. As patients of various known diagnostic classes are tested, appropriate ratio values for each diagnostic class may be determined using this technique. Based on the aforementioned study, for a lower extremity location (e.g., an ankle), a characteristic ratio within a first range (e.g., from about 0.67 to 0.73) may be employed for patients in a first diagnostic class (e.g., corresponding to severe/moderate PAD) and a characteristic ratio with a second range (e.g., from about 0.56 to 0.63) may be employed for patients in a second diagnostic class (e.g., corresponding to mild/no PAD). Based on the aforementioned study, even narrower ranges of the lower extremity characteristic ratios may be desirable (e.g., from about 0.69 to 0.71 for patients in the first diagnostic class and from about 0.57 to 0.59 for patients in the second diagnostic class). In this regard, a lower extremity characteristic ratio of about 0.70 may, for example, be used for patients in the first diagnostic class (e.g., corresponding to severe/moderate PAD) and a lower extremity characteristic ratio of about 0.58 may, for example, be used for patients for the second diagnostic class (e.g., corresponding to mild/no PAD). As used herein, in connection with a numerical range or a numeric value, the term "about" is intended to prevent restriction to a strict numerical range or exact numeric value. Rather, the term "about" is intended to describe insubstantial differences in numeric values based upon the context and technology with which the term "about" is used.

Figure 3B:
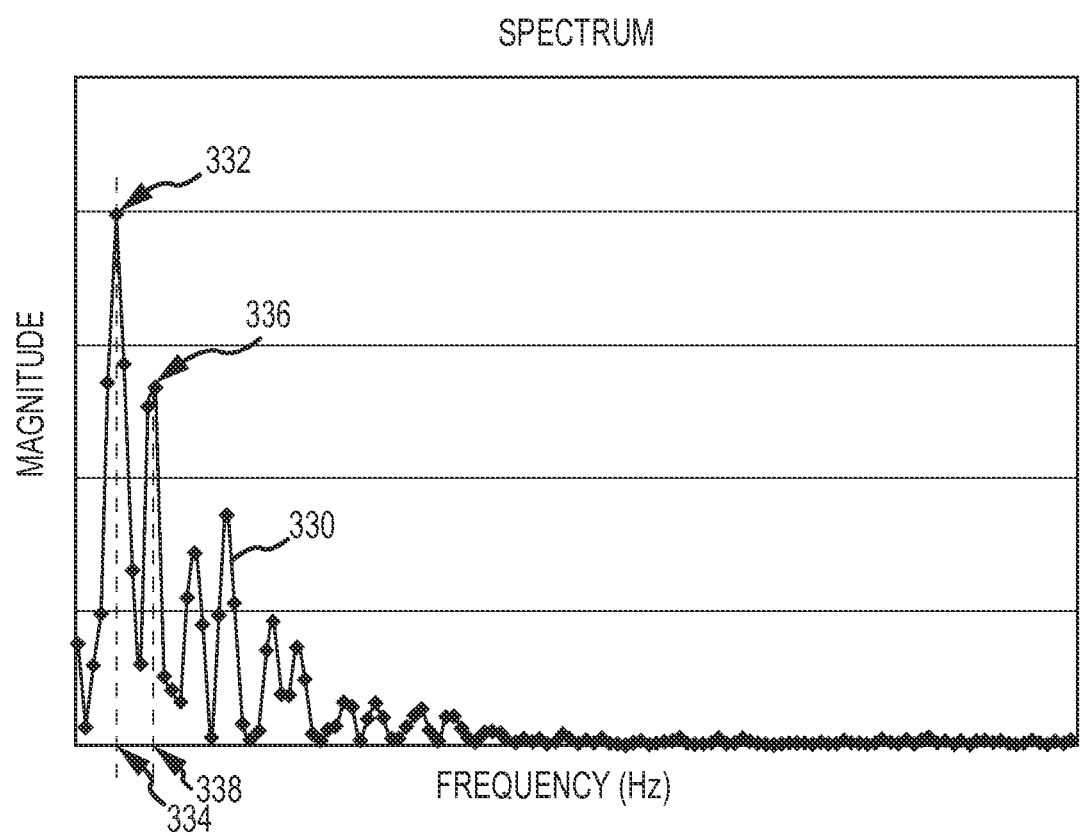
FIG. 3B is a graphical representation of an exemplary frequency domain representation of a portion the oscillometric signal of FIG. 3A within a window of interest defined in FIG. 3A.

Returning to FIG. 3A, when analyzing the oscillometric signals in accordance with the foregoing, it may be useful to perform processing on the oscillometric signal. For instance, a window of interest 390 (e.g., surrounding the maximum amplitude 340) may be defined in the oscillometric signal 320. The data from the oscillometric signal 320 within the window of interest 390 may be used to calculate a mathematical transform of the oscillometric signal 320 (e.g., the transform may produce a frequency domain representation of the oscillometric signal 320 within the window of interest 390). One example of such a transform 330 is shown in FIG. 3B. The transform 330 may be a Fourier transform (e.g., a discrete Fourier transform or a fast Fourier transform (FFT)). From the transform 330, various values may be determined that may be useful in processes that are described below. For instance, a maximum magnitude 332 of the transform 330 may be determined. The maximum magnitude 332 may occur at a fundamental frequency 334. These values are described below with greater detail with reference to FIGS. 4 and 5

Figure 4:
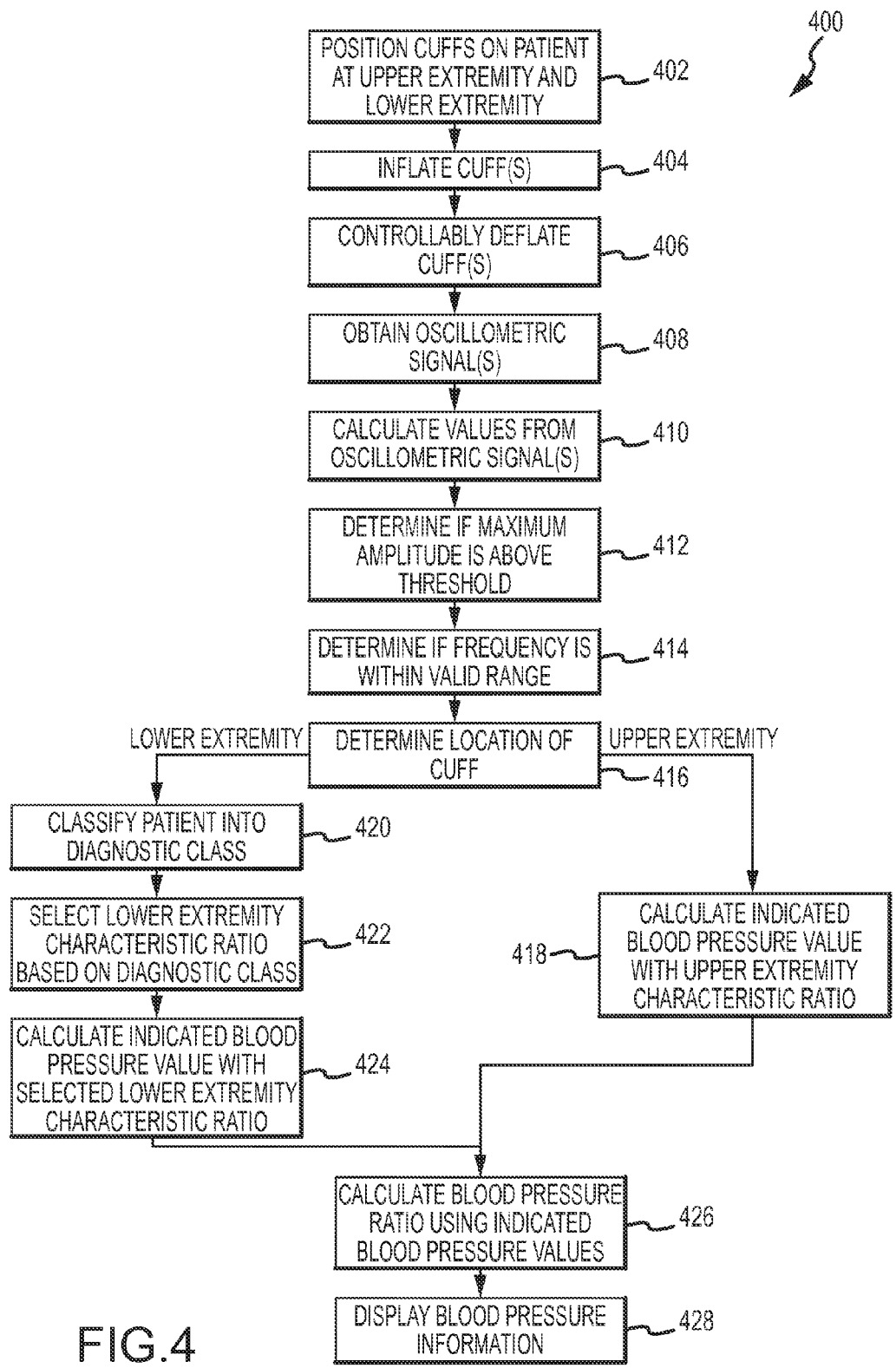
FIG. 4 depicts a flowchart of an embodiment of a process for determining one or more indicated blood pressure values in various extremities of a patient and an ABI.

FIG. 4 depicts a process 400 that may be performed to determine one or more indicated blood pressure values in a patient. One or more blood pressure cuffs (e.g., cuffs 110, 120, 130, 140 described with reference to FIGS. 1 and 2) may be positioned (402) at various locations on a patient. For instance, in one embodiment, cuffs may be positioned (402) on at least an upper extremity and a lower extremity of the patient. The cuffs may be inflated (404) to occlude blood flow in corresponding arteries adjacent to each of the cuffs. The cuffs may subsequently be controllably deflated (406). During the inflation (404) and deflation (406), the pressure in each cuff may be monitored to obtain (408) an oscillometric pressure signal corresponding to the measured pressure in each cuff as described above with reference to FIG. 3. One or more of the respective oscillometric signals may be processed such that various values may be calculated (410) for the oscillometric signals obtained at 408. For instance, a frequency and amplitude value may be calculated (410) for one or more of the oscillometric signals. With reference to FIG. 3B, the frequency may comprise the fundamental frequency 334 and the amplitude may be derived from the maximum magnitude 332. In this regard, the calculation (410) may also include calculating a transform (e.g., a discrete Fourier transform or an FFT) of one or more of the oscillometric signals.

The calculation (410) may be performed on a window of interest of an oscillometric signal. For instance, a window of interest may be identified surrounding the maximum amplitude of the oscillometric signal in the time domain. In turn, the calculation (410) may involve analyzing or performing a transform on only the portion of the oscillometric signal within the window of interest. In this regard, the calculation or processing requirements may be reduced and extraneous signals (e.g., artifacts) not likely to be useful in the processing of the oscillometric signal may be ignored from the oscillometric signal.

The process 400 may also include one or more forms of signal validation. This may help to increase the probability that the oscillometric signal to be analyzed is a valid signal. For instance, the amplitude calculated (410) may be analyzed to determine (412) if the amplitude is above some minimum threshold value. A signal that does not include an amplitude that exceeds the minimum threshold value may not be analyzable. For instance, the cuff from which the signal was obtained may not have been properly positioned on the patient or the physiology of the patient may not have produced an analyzable signal. Additionally, the frequency of the oscillometric signal may be analyzed to determine (414) if the signal has a valid frequency. The frequency of the oscillometric signal may roughly correspond to the heart rate of the patient. Thus, frequency values that are outside the bounds of a normal heart beat may indicate an oscillometric signal that is not analyzable. For instance, if the frequency is to too high or too low, the accuracy of subsequent analysis based on the oscillometric signal may be inaccurate. In one embodiment, the acceptable frequency range may be not less than about 40 oscillations per minute and not greater than about 120 oscillations per minute. Signal validation (e.g., steps 412, 416) may be performed for one or more of the oscillometric signals that are obtained.

The process 400 may also include determining (416) if the location of the cuff from which the oscillometric signal was obtained is at a lower extremity or an upper extremity of a patient. In one embodiment, dedicated cuffs may be provided for the upper extremity and the lower extremity of the patient. Also, a user may enter information regarding the cuff location.

In the case of an oscillometric signal obtained at an upper extremity, the process 400 may include calculating (418) an indicated blood pressure value for the upper extremity. This may involve multiplying the maximum amplitude value of the oscillometric signal in the time domain by an upper extremity characteristic ratio to produce an adjusted amplitude value. This adjusted amplitude value may be located within the oscillometric signal and correlated to a corresponding pressure measured in the cuff corresponding to the adjusted amplitude as shown and described above with reference to FIG. 3A. The upper extremity characteristic ratio used to calculate (418) an indicated blood pressure value for an upper extremity may, in one embodiment, be about 0.52.

In the case where it is determined (416) that the oscillometric signal originated from a lower extremity of the patient, the process 400 may include classifying (420) the patient into a diagnostic class. In one embodiment, two diagnostic classes may be established into which patients may be classified (420). The classification (420) of a patient into a diagnostic class may be based upon calculated values from the oscillometric signal obtained at the lower extremity. For instance, if the amplitude of the oscillometric signal (e.g., as determined from the magnitude at the fundamental frequency of an FFT of the portion of the oscillometric pressure signal within a window of interest) at the lower extremity is below a certain threshold, the patient may be classified (420) into a first diagnostic class, whereas if the maximum amplitude of the oscillometric signal at the lower extremity is above a certain threshold, the patient may be classified (420) into a second diagnostic class. The threshold value used to classify patients may be a fixed value (e.g., an empirically derived value) or based upon another measured or calculated value. For instance, the threshold value used in the classification (420) may, in one embodiment, be based upon the amplitude of an oscillometric signal obtained at an upper extremity of the patient. In this regard, the patient may be classified into a diagnostic class based on whether the amplitude of the oscillometric signal obtained at the lower extremity is less than or greater than a certain percentage of the amplitude of the oscillometric signal obtained at the upper extremity.

The process 400 may also include selection (422) of a selected lower extremity characteristic ratio from a plurality of ratio values for use in the calculation (424) of an indicated blood pressure value at the lower extremity. The selection (422) may be based upon the classification (420) of the patient into a diagnostic class. As an example, each diagnostic class may be correlated with a corresponding ratio value. Thus, the selection (422) may depend on the diagnostic class into which the patient is classified (420). The diagnostic classes may be based upon an indication of moderate to severe PAD in the patient for the first diagnostic class and an indication of mild to no PAD in the patient for the second diagnostic class.

In one embodiment, the first diagnostic class, corresponding to the case where the amplitude of the oscillometric signal obtained at the lower extremity falls below a threshold value, may have a corresponding ratio value not less than about 0.67 and not greater than about 0.73. For instance, the ratio value of the first diagnostic class may be in the range of about 0.69 to 0.71. In one embodiment, the ratio value for the first diagnostic class is about 0.70. The second diagnostic class, corresponding to the case where the amplitude of the oscillometric signal obtained at the lower extremity exceeds the threshold value, may have a corresponding ratio value not less than about 0.56 and not greater than about 0.63. For instance, the ratio value of the second diagnostic class may be in the range of about 0.57 to 0.59. In one embodiment, the ratio value for the second diagnostic class is about 0.58. In turn, after the selection (422) of a selected lower extremity characteristic ratio, the selected ratio may be used to calculate (426) an indicated blood pressure value at the lower extremity in a process as described above with respect to FIG. 3, wherein the characteristic ratio used is the selected lower extremity characteristic ratio.

In one embodiment, the indicated blood pressure value calculated (418) for the upper extremity and the indicated blood pressure value calculated (424) for the lower extremity may be used to further calculate (426) an EBPR. The EBPR may subsequently be displayed (428) or communicated to a user. In one embodiment, the lower extremity cuff may be located adjacent to an ankle of the patient such that the indicated blood pressure value for the lower extremity is obtained at the ankle. The upper extremity cuff may be located on an upper portion of the arm of the patient such that the indicated blood pressure value for the upper extremity is obtained for the brachial artery in the patient's arm. Thus, the calculation (426) may produce an ankle-brachial pressure index (ABI) that may in turn be used to evaluate the presence and/or severity of PAD in the patient.

In another embodiment, the process 400 shown in FIG. 4 may not involve calculation of quantitative indicated blood pressure values or blood pressure ratios. For instance, the classification (420) of the patient into a diagnostic class may provide information regarding the presence and/or severity of PAD in the patient. As stated above, classification into the first diagnostic class may be an indication of moderate to severe PAD in the patient. Thus, even if a quantitative value for an indicated blood pressure value or blood pressure ratio is not determined, the process 400 may involve indicating the class into which the patient is classified or an indication that the patient may be suffering from PAD and/or the severity of PAD in the patient. This information alone may be valuable to a user when trying to determine if and/or to what severity the patient is suffering from PAD. For instance, an indication that mild to no PAD may be presented to a user if the patient is classified (420) into the second diagnostic class and an indication of moderate to severe PAD may be presented to a user if the patient is classified (420) into the second diagnostic class regardless of whether quantitative values of indicated blood pressure or ABI are calculated.

Figure 5A:
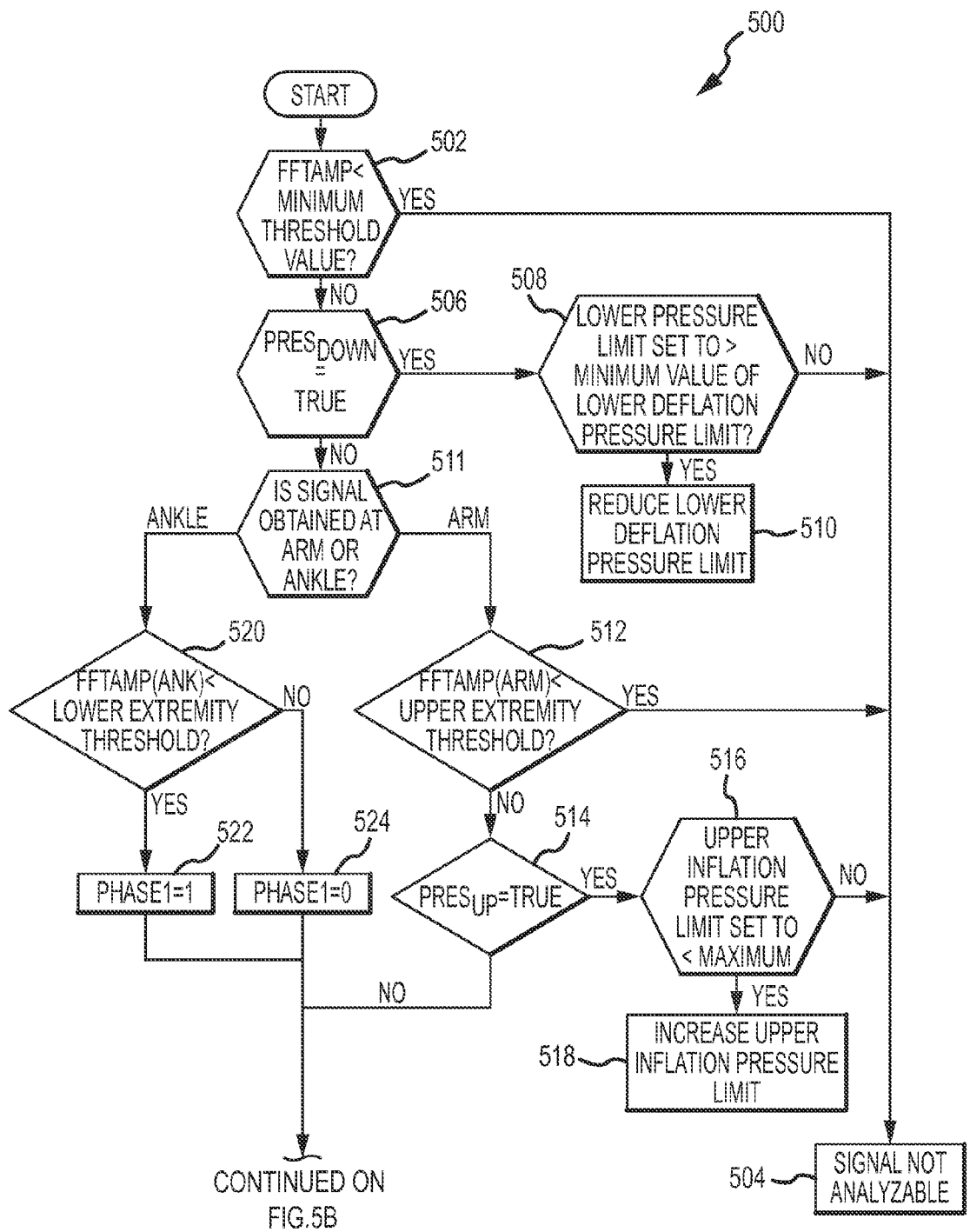
FIGS. 5A-5C depict a flowchart of another embodiment of a process for determining one or more indicated blood pressure values from an oscillometric signal.
Figure 5B:
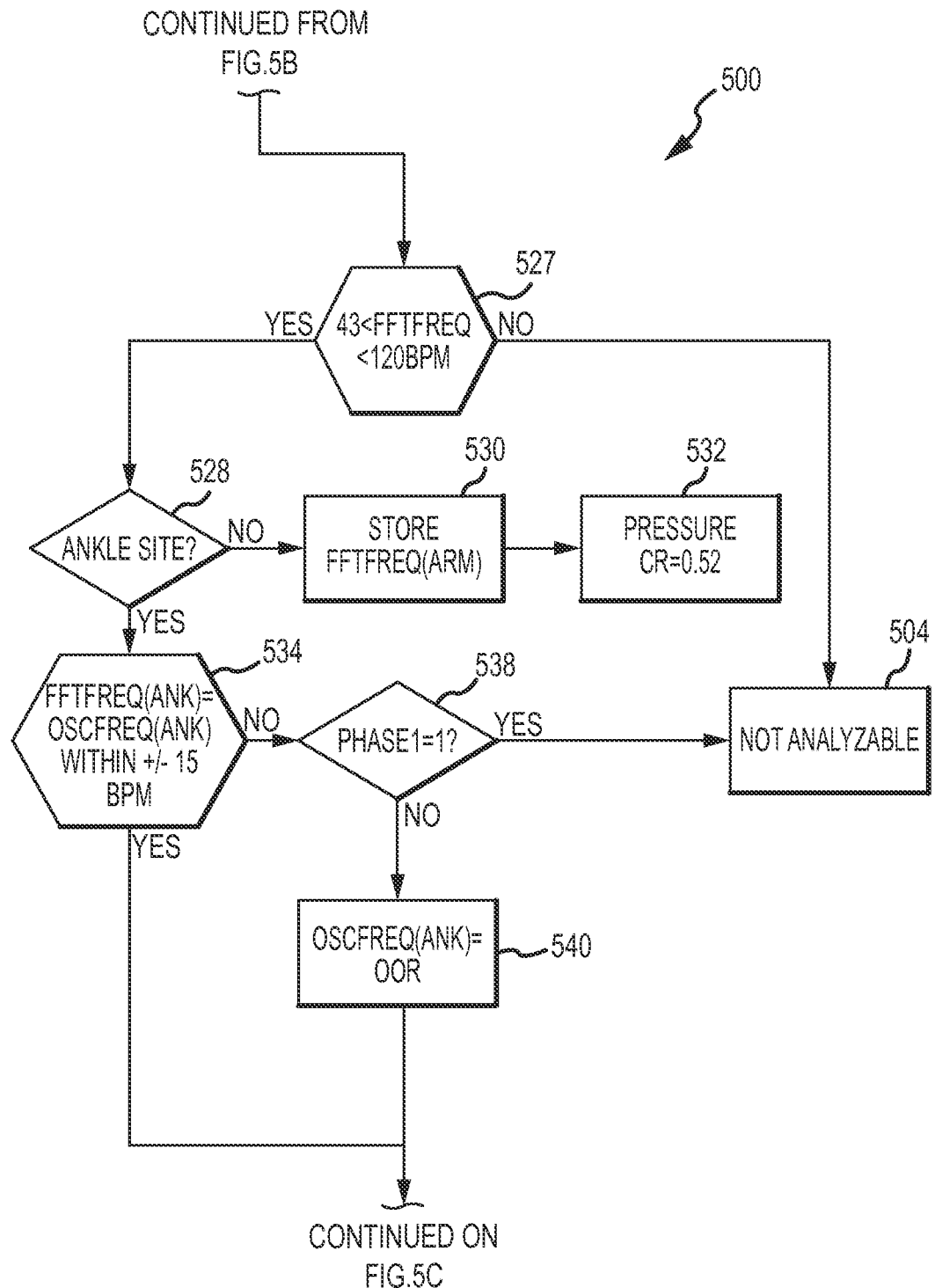
Figure 5C:
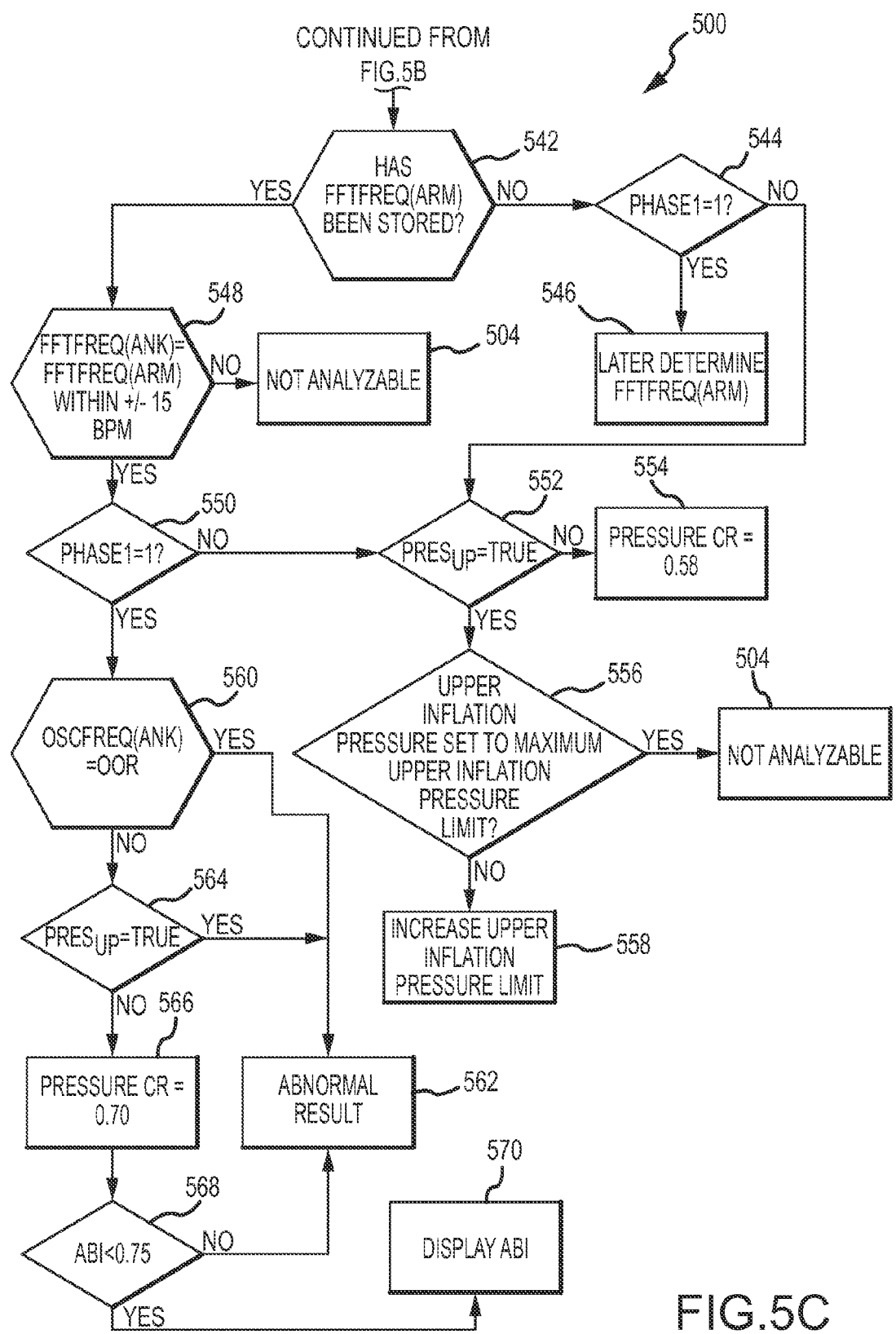

Another example of a process 500 for determining one or more indicated blood pressure values, an ABI, or an indication as to the presence and/or severity of PAD in a patient is shown in FIGS. 5A-C. The following discussion of FIGS. 5A-C may reference certain variables used in the process 500. These variables may be measured or calculated. For example, as shown and described with reference to FIG. 3B, a Fourier transform (e.g., an FFT) may be applied to an oscillometric signal to determine one or more of the variables shown and described with reference to FIGS. 5A-C. With further reference to FIGS. 3A and 3B, in one embodiment, a window of interest 390 of an oscillometric pressure signal may be analyzed to arrive at the variables used in the process 500. Variables corresponding to the upper extremity oscillometric signal may be designated with the subscript "arm," while variables corresponding to the lower extremity oscillometric signal may be designated with the subscript "ank." The value FFTamp may represent an amplitude (e.g., a maximum amplitude) at the fundamental frequency 334 of the oscillometric signal within a window of interest as determined from an FFT of the oscillometric signal. The value of FFTamp may be calculated from the maximum magnitude value 332 shown in FIG. 3B. In one embodiment, known techniques may be used to calculate the amplitude at the fundamental frequency from the maximum magnitude value 332. The amplitude at the fundamental frequency may correspond with the value FFTamp as used in the process 500. The value FFTfreq may represent the fundamental frequency 334 of the oscillometric signal within the window of interest 390 as determined from the FFT 330 of the oscillometric signal. The value OSCfreq may be the frequency of the oscillometric signal as determined by a peak detection technique in the time domain (e.g., represented as the oscillometric signal 320 with reference to FIG. 3A). The variable PRESup may correspond to a detected condition wherein the upper inflation pressure limit of the cuff was not sufficient to determine an indicated blood pressure. The variable PRESdown may correspond to a detected condition wherein the lower deflation pressure limit of the cuff was not sufficient to obtain an indicated blood pressure. One or more of the frequency variables may be calculated (e.g., during the calculation step 410 of the method depicted in FIG. 4).

Turning to FIG. 5A, the FFTamp value (e.g., derived from the oscillometric signal) may be analyzed to determine (502) if it is above a minimum threshold value. The minimum threshold value may represent the minimum amplitude required to achieve an accurate result. Furthermore, an FFTamp value below the minimum threshold value may be indicative of an incorrectly installed cuff or a patient whose physiology is such that the signal obtained at a cuff cannot be analyzed.

If the value for FFTamp is less than the minimum threshold value, the process 500 may terminate and an indication that the oscillometric signal is not analyzable may be displayed (504). Alternatively, if the FFTamp value of the oscillometric signal is above the minimum threshold value, the process may include determining (506) if a PRESdown condition was detected. As described above, the cuff may be controllably deflated through a pressure range between an upper inflation pressure limit and a lower deflation pressure limit. The PRESdown condition may be triggered when the lower deflation pressure limit to which the cuff is deflated is not sufficiently low to allow unobstructed flow of blood in the arteries adjacent to the cuff. The PRESdown condition may be detected when the oscillometric signal indicates a maximum amplitude of the signal has not yet been reached when the cuff is deflated to the lower deflation pressure limit.

If the PRESdown condition is not detected (506), the process 500 may proceed. If the PRESdown condition is detected (506), it may be determined (508) if the lower deflation pressure limit is set above a minimum value. For instance, in one embodiment, the minimum value of the lower deflation pressure limit is about 40 mmHg. If the lower deflation pressure limit is set above the minimum value, the deflation pressure limit is reduced (510) and the process 500 may be restarted with the lower deflation pressure limit reduced. If, on the other hand, the lower deflation pressure limit is at the minimum lower deflation pressure limit, the process 500 may end and an indication that the oscillometric signal is not analyzable may be displayed (504).

The process 500 may also include a determination (510) of whether the oscillometric signal being analyzed is obtained at a lower extremity or an upper extremity. As stated above, dedicated cuffs may be used to obtain upper and lower extremity measurements, and/or a user may be prompted to input the location of a given cuff.

In the case where the oscillometric signal being analyzed was obtained at an upper extremity, it may be determined (512) if the value for FFTamp(arm) is below an upper extremity threshold value specific to signals obtained at an upper extremity. The upper extremity threshold value may be a value for the amplitude of the oscillometric signal that is greater than the minimum threshold used at 502. If the FFTamp(arm) value is below the upper extremity threshold value, the process 500 may terminate and an indication that the oscillometric signal is not analyzable may be displayed (504). Again, an FFTamp(arm) value below the upper extremity threshold value may indicate that the signal in not analyzable (e.g., due to the physiology of the patient, an artifact in the signal, or an error). If, however, the value for FFTamp (arm) is above the upper extremity threshold value, the process 500 may proceed to determine (514) if a PRESup condition is detected. The PRESup condition corresponds to a case where an upper inflation pressure limit of a cuff was not sufficient to fully occlude the flow of blood in one or more arteries adjacent to the cuff. The PRESup condition may be detected when the adjusted amplitude (e.g., obtained by applying an appropriate characteristic ratio to a maximum amplitude) cannot be located in the oscillometric signal.

If a PRESup condition is detected, it is determined (516) if the upper inflation pressure limit is set below a maximum value for the upper inflation pressure limit. In one embodiment, the maximum value for the upper inflation pressure limit may be about 280 mmHg. If the upper inflation pressure limit is set at the maximum value, the process 500 may terminate and an indication that the oscillometric signal is not analyzable may be displayed (504). In contrast, if available, the upper inflation pressure limit is increased (518) and the process 500 may restart. If, at 514, it is determined that a PRESup condition was not detected, the process 500 may proceed to step 527 shown in FIG. 3B, which is described in more detail below.

In the case where it is determined (511) that the oscillometric signal is obtained at a lower extremity of the patient, the process 500 may include analyzing the oscillometric signal to determine (520) if the value for FFTamp(ank) is below a lower extremity threshold value. The lower extremity threshold value may be greater than the minimum threshold used at 502 and greater than the upper extremity threshold value used at 512. This determination (520) of whether the value of FFTamp(ank) is above or below the lower extremity threshold value may provide an indication of the presence and/or severity of PAD in the patient. An FFTamp(ank) value below the threshold value may indicate the patient belongs to a first diagnostic class (e.g., an FFTamp(ank) value below the lower extremity threshold may indicate moderate to severe PAD in the patient). In contrast, an FFTamp(ank) value above the threshold value may indicate the patient belongs to a second diagnostic class (e.g., an FFTamp(ank) value above the lower extremity threshold may indicate mild or no PAD in the patient). As described above with reference to FIG. 4, an indication as to the severity of PAD in a patient may be presented based upon the determination (520) into which diagnostic class the patient belongs. In this regard, even if a quantitative value of an indicated blood pressure value is not determined, the process 500 may include indicating to a user the diagnostic class to which the patient belongs. This information may be valuable to a user in determining the severity of PAD in the patient.

The lower extremity threshold value may be empirically derived based on an analysis of patients known to be suffering from PAD and patients known to be not suffering from PAD. In other embodiments, the lower extremity threshold value may be variable and determined by other measurements or calculations in the process 500. For instance, the lower extremity threshold value may be at least partially based on an analysis of an oscillometric pressure signal obtained at an upper extremity of the same patient. Regardless of how the lower extremity threshold value is derived or determined, the patient may be classified into a first diagnostic class 522 (characterized in FIG. 5A as Phase1=1) or a second diagnostic class 524 (characterized in FIG. 5A as Phase1=0) based upon whether the value of FFTamp(ank) is above or below the lower extremity threshold value. In any regard, the process may continue to step 527, shown in FIG. 5B.

Turning to FIG. 5B, the oscillometric signal may be analyzed to determine (527) if the oscillometric signal has a valid frequency value. The FFTfreq value (e.g., as determined using an FFT 330 of an oscillometric signal as shown with respect to FIG. 3B) may correspond with the heartbeat of the patient. Additionally, a range of values of valid frequencies may be provided for the FFTfreq value that roughly correspond to a normal range of patient heart rates. For example, the range of acceptable values for FFTfreq may be not less than about 43 oscillations (beats) per minute and not greater than about 120 oscillations (beats) per minute. If the FFTfreq value falls outside of this acceptable range, the process 500 may terminate and an indication that the oscillometric signal is not analyzable may be displayed (504). On the other hand, if the FFTfreq value is within the valid range, the process 500 may continue and it may be determined (528) if the oscillometric signal is obtained at a lower extremity.

In the case where the oscillometric signal is obtained at an upper extremity of the patient, the FFTfreq(arm) value may be stored (530) for future reference in the process as will be described further below. Furthermore, the indicated blood pressure value in the upper extremity may be calculated (532). The calculation (532) of the indicated blood pressure value in the upper extremity may use an upper extremity characteristic ratio to arrive at the indicated blood pressure value in the upper extremity. This upper extremity characteristic ratio may comprise a traditional characteristic ratio known in the art that is used to determine brachial indicted blood pressure values in an oscillometric process. As such, the upper extremity characteristic ratio may be about 0.52.

If, in contrast, it is determined (528) that the oscillometric signal is derived from a lower extremity of the patient, the process 500 may involve determining (534) if the FFTfreq (ank) value (e.g., the fundamental frequency of the signal) is equal to the OSCfreq(ank) value (e.g., the frequency of the signal using peak detection in the time domain). As stated above, the OSCfreq(ank) value may be derived using a technique applied to the oscillometric signal different from the technique applied to the oscillometric signal used to determine FFTfreq(ank). In this regard, the determining (534) may provide additional means of signal validation. For example, if the two values are not equal, it may indicate some signal corruption (e.g., due to an artifact, noise, etc.). If the two values are within plus or minus a specified number of oscillations (beats) per minute (e.g., +/−15 beats per minute), the two values may be determined to be equal and the process 500 may proceed to step 542 shown in FIG. 5C, which is described in more detail below.

If the FFTfreq(ank) and OSCfreq(ank) values are not equal, and it is determined (538) that the patient was classified into the first diagnostic class 522, the process 500 may terminate and an indication that the oscillometric signal is not analyzable may be displayed (504). This may be because the oscillometric pressure signal derived from a patient may not have characteristics sufficient to continue the process 500 to arrive at reliable results. Moreover, the classification of the patient into the first diagnostic class 522 may provide a reliable indication as to the presence and/or severity of PAD in the patient. Thus, as described above, an indication as to the presence and/or severity of PAD in the patient or an indication of abnormal results may be displayed without quantitative values. If, instead the patient is not in the first diagnostic class 522, the OSCfreq(ank) value may be indicated (540) as being out of range. The indication (540) that OSCfreq(ank) is out of range may be used elsewhere in the process 500. In any regard, the process may proceed to step 542 shown in FIG. 5C. The process 500 may continue in the case of the patient being classified into the second diagnostic class 524 because the derived signal may have characteristics that are more likely to produce reliable results.

Turning to FIG. 5C, it may be determined (542) if a valid value for FFTfreq(arm) has been stored at 530 in FIG. 5B. If no FFTfreq(arm) value has been stored, it may be determined (544) if the patient has been classified into the first diagnostic class 522. If the patient is in the first diagnostic class 522, the process may be suspended (546) until an FFTfreq(arm) value is later determined (e.g., on a subsequent cycle of one of the upper extremity cuffs). If the patient is not in the first diagnostic class 522, the process 500 may continue to step 552 which is described in greater detail below.

If it is determined (542) that an FFTfreq(arm) value has been stored, the process 500 may proceed with a determination (548) as to whether the FFTfreq(ank) value is equal to the FFTfreq(arm) value that was stored. The comparison of these frequency values for the upper extremity and the lower extremity may provide an indication as to whether the cuffs are correctly positioned on a patient or whether an error has occurred. As the FFTfreq(arm) and FFTfreq(ank) values may both be dependent upon the heart rate of the patient, these two values are likely not to be significantly different for a normal patient where the cuffs are correctly placed. In the instance that these values are significantly different (e.g., more than +/−15 oscillations per minute apart), it may be that the cuffs are not correctly positioned or not positioned on the patient at all. However, if the values are within, for example, +/−15 oscillations per minute, the signals may be deemed to be equal. If the values of FFTfreq(ank) and FFTfreq(arm) are not equal, the process 500 may terminate and an indication that the oscillometric signal is not analyzable may be displayed (504). In contrast, if the values are equal, it may be determined (550) into which diagnostic class the patient is classified for the purpose of selecting an appropriate selected lower extremity characteristic ratio that may in turn be used to determine an indicated blood pressure value.

If the patient is in the second diagnostic class 524 as described at either of steps 544 or 550, the process 500 may include determining (552) if a PRESup condition is detected. If the PRESup condition is not detected, the characteristic ratio for the second diagnostic class may be selected and an indicated blood pressure value may be calculated (554) using the selected lower extremity characterization ratio (e.g., of about 0.58 for the second diagnostic class). If a PRESup condition is detected, it may be determined (556) if the upper inflation pressure limit for the cuff is set to the maximum value for the upper inflation pressure limit. If the upper inflation pressure limit is set to the maximum value, the process 500 may terminate and an indication that the oscillometric signal is not analyzable may be displayed (504). If the upper inflation pressure limit is not set to the maximum value, the upper inflation pressure limit may be increased (558) and the process may restart.

If it is determined (550) that the patient is in the first diagnostic class 522, it may be determined (560) if the OSCfreq(ank) value is out of range as determined at 540 with reference to FIG. 5B. If the value for OSCfreq(ank) is out of range, the process 500 may include indicating (562) the process resulted in an abnormal result. This may be an indication that in the patient is likely suffering from PAD. The indication (562) that the patient is likely suffering from PAD may not include a quantitative indicated blood pressure value for the lower extremity, but rather may indicate, based on the oscillometric signal analysis, an abnormal result may provide some indication as to the severity of PAD in the patient.

If, on the other hand, the value for OSCfreq(ank) is not out of range, it may be determined (564) if a PRESup condition is detected. If a PRESup condition is detected, the process 500 may include indicating (562) the severity of PAD in the patient. Again, the indication (562) may not include a quantitative value for an indicated blood pressure value in the lower extremity of the patient. If a PRESup condition was not detected, a selected lower extremity characteristic ratio of about 0.7 may be selected (568). This selected lower extremity characteristic ratio may be used to calculate an indicated blood pressure value for the lower extremity. The indicated blood pressure value for the lower extremity may in turn be used with an indicated blood pressure value for the upper extremity (e.g., as arrived at using the characteristic ratio determined at step 532) to calculate an ABI value. It may be determined (566) if the calculated ABI value is greater than 0.75. If so, an indication (562) of PAD may be presented (e.g., without displaying the quantified value of the calculated ABI). If the patient's ABI value is determined (566) to be less than 0.75, the calculated ABI may be displayed (570) to a user.

Figure 6:
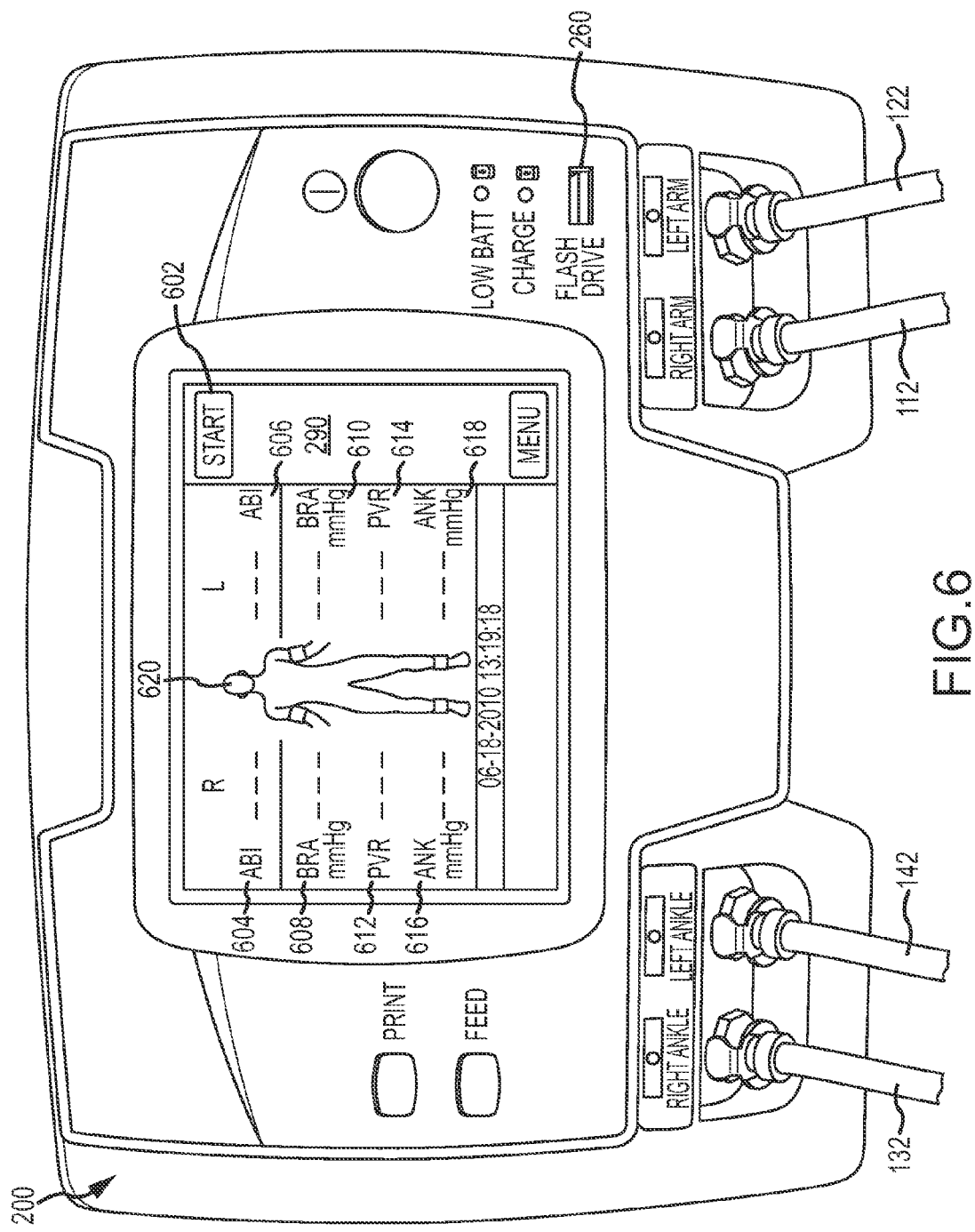
FIG. 6 is a front view of embodiment of a device operable to determine one or more indicated blood pressure values in various extremities of a patient and an ABI.

FIG. 6 depicts one embodiment of a control module 200 where a display 290 thereof can be seen. FIG. 6 also shows the connection of pneumatic tubes 112, 122, 132, and 142 to the control module 200. Furthermore, a removable storage interface 260 can be seen. In the embodiment depicted in FIG. 6, the removable storage interface 260 may comprises a USB port capable of receiving a removable storage device (e.g., a flash drive).

The display 290 may also include a "START" button 602 to initiate performance of a process (e.g. the process 400 and/or process 500 shown and described with respect to FIGS. 4 and 5, respectively) to obtain an oscillometric signal at each of one or more cuffs (e.g., as shown with reference to FIGS. 1 and 2). The display 290 may also include a display of values for right ABI 604 and left ABI 606. Additionally, values for the right upper extremity indicated blood pressure value 608 and left upper extremity indicated blood pressure value 610 may be displayed, if determined. Further still, the right lower extremity indicated blood pressure value 616 and the left lower extremity indicated blood pressure value 608 may be displayed, if determined. Also, the control module 200 may display additional patient information (e.g., left and right pulmonary vascular resistance (PVR) values).

Figure 7A:
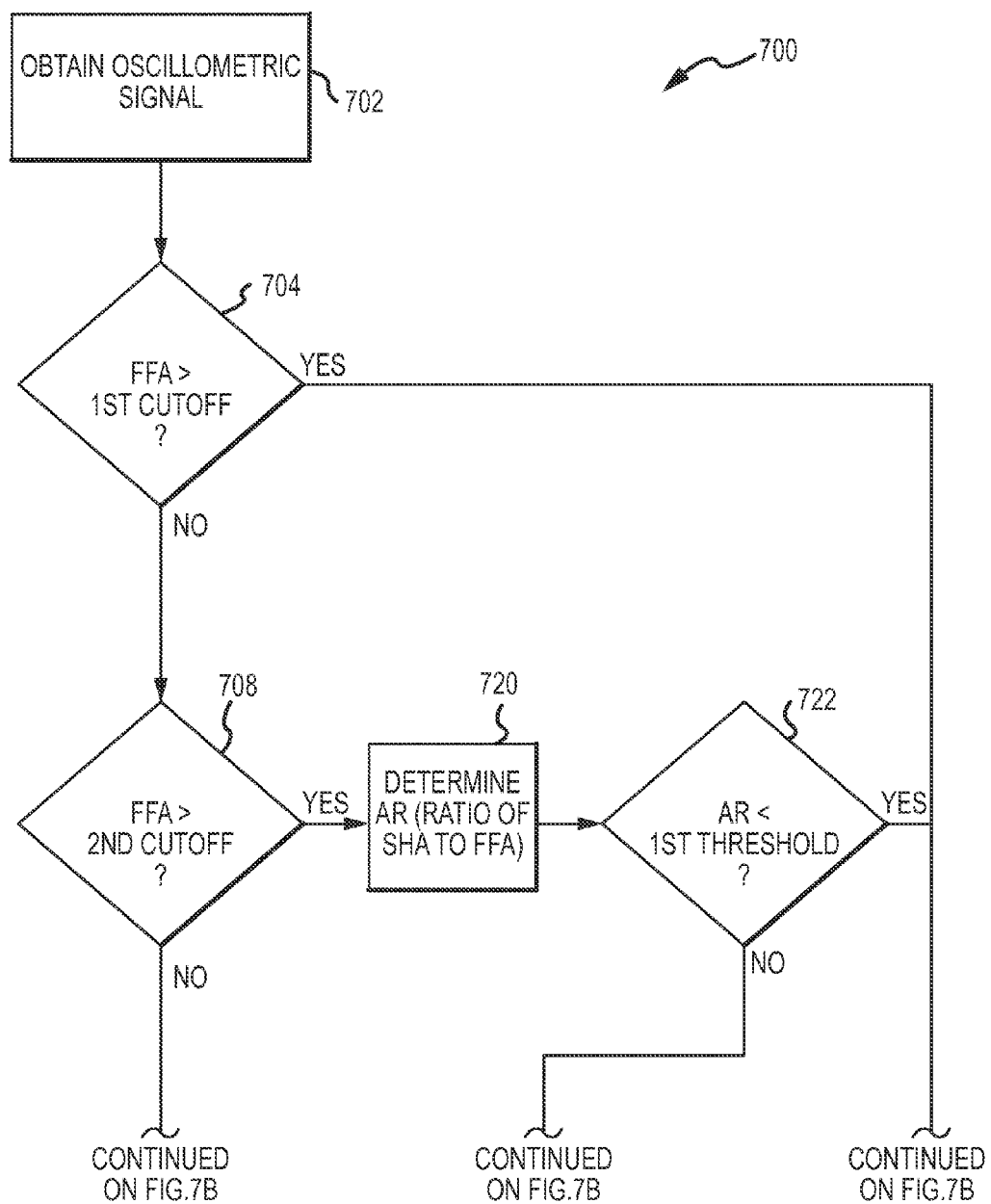
FIGS. 7A-7B depict a flowchart of an embodiment of a process for evaluating whether an oscillometric signal representative of pressure oscillations in the vasculature of a patient is associated with special conditions.
Figure 7B:
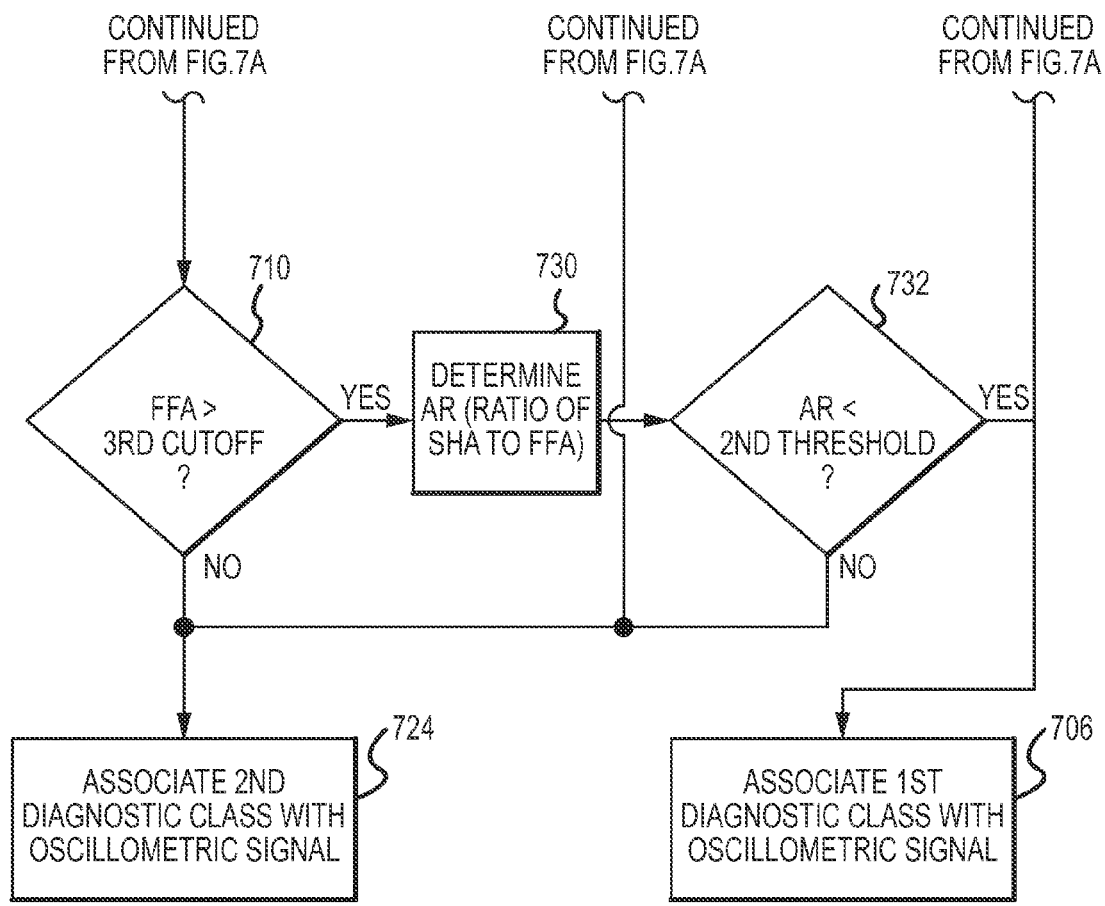

FIGS. 7A-7B depict the steps involved in one embodiment of a process 700 for evaluating whether an oscillometric signal representative of pressure oscillations in the vasculature of a patient is associated with special conditions. The special conditions may, for example, include the oscillometric signal being associated with a loosely wrapped pressure cuff and/or the oscillometric signal being associated with the patient having particularly thin ankles. In this regard, where a healthy patient has particularly thin ankles and/or where the pressure cuff used to occlude blood flow in the patient's lower extremity has been wrapped too loosely, the amplitude of the lower extremity oscillometric signal at the fundamental frequency may be below a cutoff value established for patients who are classified as having peripheral arterial disease. Unless further analysis of the lower extremity oscillometric signal is conducted, this can result in an otherwise healthy patient being inadvertently classified as having disease or the oscillometric signal being considered non-analyzable. The special conditions evaluation process 700 of FIG. 7A-7B may be implemented to further evaluate an oscillometric signal to identify whether the oscillometric signal is associated with special conditions and, if so, associate the signal with the proper diagnostic class for further evaluation of the patient's indicated blood pressure value(s) and/or ABI.

The special conditions evaluation process 700 of FIGS. 7A-7B may, for example, be implemented within a control module 200 such as shown in FIG. 2 of a system 100 such as shown in FIG. 1 that is operable to determine one or more indicated blood pressure values in a patient 150. In this regard, process 700 may comprise a special conditions analysis module 290 included in control module 200 of system 100. The special conditions analysis module 290 may be provided as hardware (e.g., ASICs, FPGAs, etc.) and/or as software in the form of machine readable code stored on the memory 270 of control module 200 and executable by the processor 250 of the control module 200, such as depicted in FIG. 2. Additionally, the special conditions evaluation process 700 may be included in a process such as process 500 for determining one or more indicated blood pressure values, an ABI, or an indication as the to the presence and/or severity of peripheral arterial disease such as shown in FIGS. 5A-5C. For example, one or more steps of the special conditions evaluation process 700 may be performed between steps 520 and 522/524 of the process 500 of FIGS. 5A-5C.

The special conditions evaluation process 700 may be initiated with obtaining (702) an oscillometric signal at a location on an extremity of the patient. The extremity may, for example, be a lower leg of the patient, and more specifically, may, for example, be the ankle of the patient. In one implementation, step 702 may, for example, coincide with obtaining (408) an oscillometric signal in a process (400) of determining one or more indicated blood pressure values in a patient such as shown in FIG. 4, and obtaining (702) the oscillometric signal may be preceded by positioning one or more cuffs at one or more locations (e.g. an ankle) on the patient, inflating the cuff(s), and controllably deflating the cuff(s).

A value associated with a first frequency component of the oscillometric signal is compared (704) to a first cutoff value. In one implementation, step 704 may, for example, coincide with step 520 of process 500 shown in FIGS. 5A-5C. The value associated with the first frequency component of the oscillometric signal may, for example, be an amplitude value associated with a fundamental frequency of a frequency domain representation of the oscillometric signal. In this regard, the frequency domain representation of the oscillometric signal may be obtained through the use of a Fourier transformation operation (e.g., a discrete Fourier transform or a fast Fourier transform (FFT)) applied to the time domain oscillometric signal. The fundamental frequency may be identified as the frequency associated with the maximum amplitude (the largest peak) in the frequency domain representation of the oscillometric signal. FIG. 3B shows an exemplary frequency domain representation (spectrum) of an oscillometric signal having a maximum amplitude value 332 associated with the fundamental frequency 334. Such maximum amplitude value may be referred to herein as the 'fundamental frequency amplitude' or 'FFA'.

When a first outcome results from the comparison (704) of the value associated with the first frequency component to the first cutoff value (e.g., when the FFA is greater than the first cutoff value), a first diagnostic class is associated (706) with the oscillometric signal (e.g. the patient may be classified as belonging in a first diagnostic class). Where the special conditions evaluation process 700 is part of a process 500 such as shown in FIGS. 5A-5C, step 706 may coincide with step 524 (characterized in FIG. 5A as Phase1=0). Thereafter, the special conditions evaluation process 700 is concluded and the process 500 may be continued.

When a second outcome results from the comparison (704) of the value associated with the first frequency component to the first cutoff value (e.g., when the FFA is less than or equal to the first cutoff value), the value associated with the first frequency component is then compared (708) to a second cutoff value different from the first cutoff value. In this regard, the second cutoff value may be a lower cutoff value than the first cutoff value.

When a first outcome results from the comparison (708) of the value associated with the first frequency component to the second cutoff value (e.g., when the FFA is greater than the second cutoff value), steps 720 and 722 are performed. In step 720, a ratio of a value associated with a second frequency component of the oscillometric signal to the value associated with a first frequency component of the oscillometric signal is determined (720). In this regard, the value associated with the second frequency component of the oscillometric signal may, for example, be a secondary maximum amplitude value (the second largest peak) associated with a second harmonic frequency of the frequency domain representation of the oscillometric signal. In the exemplary frequency domain representation (spectrum) of FIG. 3B, the secondary maximum amplitude value 336 is associated with the second harmonic frequency 338. Such secondary maximum amplitude value may be referred to herein as the 'second harmonic amplitude' or 'SHA', and the ratio may be referred to herein as the 'amplitude ratio' or 'AR' and may be computed in accordance with the expression AR=SHA/FFA.

In step 722, the ratio determined in step 720 is compared (722) to a first threshold value. When a first outcome results from the comparison (722) of the ratio determined in step 720 to the first threshold value (e.g., when AR is less than the first threshold value), step 706 is undertaken wherein the first diagnostic class is associated (706) with the oscillometric signal. Thereafter, the special conditions evaluation process 700 is concluded (and process 500 may be continued).

When a second outcome results from the comparison (722) of the ratio determined in step 720 to the first threshold value (e.g., when AR is greater than or equal to the first threshold value), a second diagnostic class is associated (724) with the oscillometric signal (e.g. the patient may be classified as belonging in a second diagnostic class). Where the special conditions evaluation process 700 is part of a process 500 such as shown in FIGS. 5A-5C, step 724 may coincide with step 522 (characterized in FIG. 5A as Phase1=1). Thereafter, the special conditions evaluation process 700 is concluded and the process 500 may be continued.

When a second outcome results from the comparison (708) of the value associated with the first frequency component to the second cutoff value (e.g., when FFA is less than or equal to the second cutoff value), the value associated with the first frequency component is compared (710) to a third cutoff value different from the first and second cutoff values. In this regard, the third cutoff value may be a lower cutoff value than the second cutoff value.

When a first outcome results from the comparison (710) of the value associated with the first frequency component to the third cutoff value (e.g., when the FFA is greater than the third cutoff value), steps 730 and 732 are performed. In step 730, a ratio of the value associated with the second frequency component of the oscillometric signal (e.g., the SHA) to the value associated with a first frequency component (e.g., the FFA) of the oscillometric signal is determined (720). In this regard, step 730 is similar to step 720 and may be undertaken by the same implemented portion of the process 700 if desired (e.g., AR=SHA/FFA).

In step 732, the ratio determined in step 730 is compared (732) to a second threshold value different from the first threshold value used in comparison (722). In this regard, the second threshold value used in comparing step 732 may be greater than the first threshold value used in comparing step 722.

When a first outcome results from the comparison (732) of the ratio determined in step 730 to the second threshold value (e.g., when AR is less than the second threshold value), the first diagnostic class may be associated (706) with the oscillometric signal, and thereafter, the special conditions evaluation process 700 is concluded (and process 500 may be continued). When a second outcome results from the comparison (732) of the ratio determined in step 730 to the second threshold value (e.g., when AR is greater than or equal to the second threshold value), the second diagnostic class may be associated (724) with the oscillometric signal, and thereafter, the special conditions evaluation process 700 is concluded (and process 500 may be continued).

When a second outcome results from the comparison (710) of the value associated with the first frequency component to the third cutoff value (e.g., when FFA is less than or equal to the third cutoff value), the second diagnostic class is associated (724) with the oscillometric signal, and thereafter, the special conditions evaluation process 700 is concluded (and process 500 may be continued).

One or more of the first threshold value, second threshold value, first cutoff value, second cutoff value and third cutoff value may be empirically derived values obtained using data collected from a sample population of patients. FIG. 8 shows a plot of the FFA versus AR for an exemplary set of data obtained from a sample population of patients. In the plot of FIG. 8, the FFA values ranged from 0.066 to 0.168 volts for the particular equipment (e.g., a Vantage unit produced by Summit Doppler Systems, Inc. of Golden, Colo. and a Hokanson PV cuff) used when obtaining oscillometric signals from the sample population of patients. Based on the exemplary data shown in FIG. 8, the first threshold value was selected to be an AR of 45%, the second threshold was selected to be and AR of 55%, the first cutoff value was selected to be an FFA of 0.156 volts, the second cutoff value was selected to be an FFA of 0.110 volts, and the third cutoff value was selected to be an FFA of 0.085 volts. In this regard, the first threshold AR of 45% was selected based on it being proximal to and greater than the highest AR ratios obtained for oscillometric signals with fundamental frequency amplitudes between the first and second cutoffs. The second threshold AR of 55% was selected based on it being proximal to and greater than the highest AR ratios obtained for oscillometric signals with fundamental frequency amplitudes between the second and third cutoffs.

While various embodiments of the present invention have been described in detail, further modifications and adaptations of the invention may occur to those skilled in the art. However, it is to be expressly understood that such modifications and adaptations are within the spirit and scope of the present invention.

What is claimed is:

1. A method for evaluating whether an oscillometric signal representative of pressure oscillations in the vasculature of a patient is associated with special conditions, said method comprising:
   obtaining, from a blood pressure cuff, an oscillometric signal at a location on an extremity of the patient;
   determining, using a processor, a ratio using a value associated with a first frequency component of the oscillometric signal and a value associated with a second frequency component of the oscillometric signal;
   comparing, using the processor, the ratio to a threshold value;
   associating, using the processor, a first diagnostic class from a plurality of diagnostic classes with the oscillometric signal when a first outcome of the comparison to the threshold value results from said comparing the ratio to a threshold value;
   associating, using the processor, a second diagnostic class from a plurality of diagnostic classes with the oscillometric signal when a second outcome of the comparison to the threshold value results from said comparing the ratio to a threshold value, wherein the first diagnostic class is characterized as the patient having a first severity of peripheral arterial disease and the second diagnostic class is characterized as the patient having a second severity of peripheral arterial disease;
   selecting, using the processor, a characteristic ratio based on the diagnostic class associated with the oscillometric signal;
   applying, using the processor, the characteristic ratio to a maximum amplitude of the oscillometric signal to determine an adjusted amplitude value of the oscillometric signal; and
   correlating, using the processor, the adjusted amplitude value of the oscillometric signal to a pressure in the blood pressure cuff to determine an indicated blood pressure value for the patient.

2. The method according to claim 1, wherein the extremity comprises a lower extremity.

3. The method according to claim 2, wherein the location on the lower extremity comprises an ankle.

4. The method according to claim 1 wherein the first outcome of the comparison to the threshold value comprises the ratio being less than the threshold value, and wherein the second outcome of the comparison to the threshold value comprises the ratio being greater than or equal to the threshold value.

5. The method according to claim 1 further comprising:
   transforming the oscillometric signal from a time domain representation into a frequency domain representation; and
   identifying the first frequency component and the second frequency component from the frequency domain representation of the oscillometric signal.

6. The method according to claim 5 wherein said transforming the oscillometric signal comprises performing a Fourier transform operation.

7. The method according to claim 5 wherein the value associated with the first frequency component comprises an amplitude of the first frequency component in the frequency domain, and wherein the value associated with the second frequency component comprises an amplitude of the second frequency component in the frequency domain.

8. The method according to claim 5 wherein the first frequency component comprises the fundamental frequency of the oscillometric signal in the frequency domain and wherein the second frequency component comprises the second harmonic frequency of the oscillometric signal in the frequency domain.

9. The method according to claim 1 wherein said steps of said method are included within a process for evaluating the presence of peripheral arterial disease in a patient using an oscillometric signal obtained at a lower extremity of the patient.

10. A system operable to evaluate whether an oscillometric signal representative of pressure oscillations in the vasculature of a patient is associated with special conditions, said system comprising:
   a pressure applicator positionable at a location on an extremity of a patient, said pressure applicator being controllable to apply a pressure to occlude blood flow in a portion of the extremity and to reduce the pressure applied thereby to permit blood flow to return in the portion of the extremity;
   a processor in operative communication with said pressure applicator;
   a pressure transducer in operative communication with said pressure applicator to obtain an oscillometric signal from the extremity as pressure applied by the pressure applicator to the extremity is reduced, wherein said pressure transducer is in operative communication with said processor; and
   a special conditions evaluation module executable by said processor, said special conditions evaluation module being operable to:
   determine a ratio using a value associated with a first frequency component of the oscillometric signal and a value associated with a second frequency component of the oscillometric signal;
   compare the ratio to a threshold value;
   associate a first diagnostic class from a plurality of diagnostic classes with the oscillometric signal when a first outcome of the comparison to the threshold value results from comparing the ratio to a threshold value;
   associate a second diagnostic class from a plurality of diagnostic classes with the oscillometric signal when a second outcome of the comparison to the threshold value results from comparing the ratio to a threshold value, wherein the first diagnostic class is characterized as the patient having a first severity of peripheral arterial disease and the second diagnostic class is characterized as the patient having a second severity of peripheral arterial disease;
   select a characteristic ratio based on the diagnostic class associated with the oscillometric signal;
   apply the characteristic ratio to a maximum amplitude of the oscillometric signal to determine an adjusted amplitude value of the oscillometric signal; and
   correlate the adjusted amplitude value of the oscillometric signal to a pressure in the pressure applicator to determine an indicated blood pressure value for the patient.

11. A computer program product for evaluating whether an oscillometric signal representative of pressure oscillations in the vasculature of a patient is associated with special conditions, said computer program product comprising:
   a non-transitory computer readable medium having computer readable program code embodied therein, the computer readable program code including:
   computer readable program code enabling a processor to obtain, from a blood pressure cuff, an oscillometric signal at a location on an extremity of the patient;
   computer readable program code enabling a processor to determine a ratio using a value associated with a first frequency component of the oscillometric signal and a value associated with a second frequency component of the oscillometric signal;
   computer readable program code enabling a processor to compare the ratio to a threshold value;
   computer readable program code enabling a processor to associate a first diagnostic class from a plurality of diagnostic classes with the oscillometric signal when a first outcome of the comparison to the threshold value results from comparing the ratio to a threshold value;
   computer readable program code enabling a processor to associate a second diagnostic class from a plurality of diagnostic classes with the oscillometric signal when a second outcome of the comparison to the threshold value results from comparing the ratio to a threshold value, wherein the first diagnostic class is characterized as the patient having a first severity of peripheral arterial disease and the second diagnostic class is characterized as the patient having a second severity of peripheral arterial disease;
   computer readable program code enabling a processor to select a characteristic ratio based on the diagnostic class associated with the oscillometric signal;
   computer readable program code enabling a processor to apply the characteristic ratio to a maximum amplitude of the oscillometric signal to determine an adjusted amplitude value of the oscillometric signal; and
   computer readable program code enabling a processor to correlate the adjusted amplitude value of the oscillometric signal to a pressure in the blood pressure cuff to determine an indicated blood pressure value for the patient.

* * * * *